(12) United States Patent
Hollenbach et al.

(10) Patent No.: US 8,304,521 B2
(45) Date of Patent: Nov. 6, 2012

(54) PHOSPHO-SPECIFIC ANTI-PAX3 ANTIBODIES

(75) Inventors: Andrew D. Hollenbach, New Orleans, LA (US); Patrick J. Miller, New Orleans, LA (US); Kevin N. Dietz, New Orleans, LA (US)

(73) Assignee: Board of Supervisors of Louisiana State University And Agricultural and Mechanical College, Baton Rouge, LA (US)

( * ) Notice: Subject to any disclaimer, the term of this patent is extended or adjusted under 35 U.S.C. 154(b) by 272 days.

(21) Appl. No.: 12/477,541

(22) Filed: Jun. 3, 2009

(65) Prior Publication Data

US 2009/0298083 A1    Dec. 3, 2009

Related U.S. Application Data

(60) Provisional application No. 61/058,388, filed on Jun. 3, 2008.

(51) Int. Cl.
*C07K 5/00* (2006.01)
*G01N 33/53* (2006.01)

(52) U.S. Cl. .......... 530/352; 436/517; 436/547; 436/35; 435/7.1; 530/324

(58) Field of Classification Search .................. 435/7.1, 435/214; 436/548, 517, 547, 35; 536/324, 536/352; 530/324, 352
See application file for complete search history.

(56) References Cited

U.S. PATENT DOCUMENTS 4,444,879 A * 4/1984 Foster et al. ................. 435/7.95

OTHER PUBLICATIONS

Lam et al. The Oncogenic Potential of the Pax3-FKHR Fusion Protein Requires the Pax3 Homeodomain Recognition Helix but Not the Pax3 Paired-Box DNA Binding Domain, Molecular and Cellular Biology 19 (1): 594-601 (Jan. 1999).*
Miller et al. The oncogenic fusion protein Pax3-FKHR has a greater post-translational stability relative to Pax3 during early myogenesis, Biochimica et Biophysica Acta 1770 1450-1458 (2007).*
Amstutz et al. Phosphorylation regulates transcriptional activity of PAX3/FKHR and reveals novel therapeutic possibilities, Cancer Res, vol. 68: pp. 3767-3776 (May 15, 2008).*
Boutet, S.C. et al., "Regulation of Pax3 by proteasomal degradation of monoubiquitinated protein in skeletal muscle progenitors," *Cell*, vol. 130, pp. 349-362 (2007).
Boyle, W.J. et al., "Phosphopeptide mapping and phosphoamino acid analysis by two-dimensional separation on thin-layer cellulose plates," *Method Enzymol*, vol. 201, pp. 110-149 (1991).
Buckingham, M. et al., "The role of Pax genes in the development of tissues and organs: Pax3 and Pax7 regulate muscle progenitor cell functions," *Annual review of cell and developmental biology*, vol. 23, pp. 645-673 (2007).
Epstein, J.A. et al., "Pax3 modulates expression of the c-Met receptor during limb muscle development," *Proc Natl Acad Sci U S A*, vol. 93, pp. 4213-4218 (1996).
Ho, S.N. et al., "Site-directed mutagenesis by overlap extension using the polymerase chain reaction," *Gene*, vol. 77, pp. 51-59 (1989).
Hollenbach, A.D. et al., "The EF-hand calcium-binding protein calmyrin inhibits the transcriptional and DNA-binding activity of Pax3," *Biochim Biophys Acta*, vol. 1574, pp. 321-328 (2002).
Hollenbach, A.D. et al., "The Pax3-FKHR oncoprotein is unresponsive to the Pax3-associated repressor hDaxx," *Embo J*, vol. 18, pp. 3702-3711 (1999).
Hunter, T. et al., "The regulation of transcription by phosphorylation," *Cell*, vol. 70, pp. 375-387 (1992).
Kitzmann, M. et al., "cdk1- and cdk2-mediated phosphorylation of MyoD Ser200 in growing C2 myoblasts: role in modulating MyoD half-life and myogenic activity," *Mol Cell Biol*, vol. 19, pp. 3167-3176 (1999).
Laker, C. et al., "Host cis-mediated extinction of a retrovirus permissive for expression in embryonal stem cells during differentiation," *Journal of virology*, vol. 72, pp. 339-348 (1998).
Lam, P.Y. et al., "The oncogenic potential of the Pax3-FKHR fusion protein requires the Pax3 homeodomain recognition helix but not the Pax3 paired-box DNA binding domain," *Mol Cell Biol*, vol. 19, pp. 594-601 (1999).
Li, L. et al., "FGF inactivates myogenic helix-loop-helix proteins through phosphorylation of a conserved protein kinase C site in their DNA-binding domains," *Cell*, vol. 71, pp. 1181-1194 (1992).
Magnaghi, P. et al., "HIRA, a mammalian homologue of *Saccharomyces cerevisiae* transcriptional co-repressors, interacts with Pax3," *Nat Genet*, vol. 20, pp. 74-77 (1998).
Maroto, M. et al., "Ectopic Pax-3 activates MyoD and Myf-5 expression in embryonic mesoderm and neural tissue," *Cell*, vol. 89, pp. 139-148 (1997).
Miller, P.J. et al., "The oncogenic fusion protein Pax3-FKHR has a greater post-translational stability relative to Pax3 during early myogenesis," *Biochimica et biophysica acta*, vol. 1770, pp. 1450-1458 (2007).
Miller, P.J. et al., "Identification of serine 205 as a site of phosphorylation on Pax3 in proliferating but not differentiating primary myoblasts," Protein Science, vol. 17, pp. 1979-1986 (2008).
Rando, T.A. et al., "Methods for myoblast transplantation," *Methods in cell biology*, vol. 52, pp. 261-272 (1997).
Swift, S. et al., "Rapid production of retroviruses for efficient gene delivery to mammalian cells using 293T cell-based systems," in *Current Protocols in Immunology*. (eds. J.E. Coligan, A.M. Kruisbeek, D.H. Margulies, E.M. Shevach, and W. Strober), pp. 10.17. John Wiley and Sons, Boston, MA (1999).

(Continued)

*Primary Examiner* — Gail R Gabel
(74) *Attorney, Agent, or Firm* — Bonnie J. Davis; John H. Runnels

(57) ABSTRACT

Pax3, a member of the paired class homeodomain family of transcription factors and an essential protein for early skeletal muscle development, was shown to be phosphorylated in proliferating mouse primary myoblasts. Furthermore, Ser205, Ser201 and Ser209 were identified as the only sites of phosphorylation on Pax3 in proliferating mouse primary myoblasts. Phosphorylation of Ser205 was shown to be required for the efficient phosphorylation of Ser201 and/or Ser209. Site-specific antibodies were made to each of these three sites when phosphorylated. These three sites are also present and phosphorylated in the Pax3-FOXO1 fusion protein, and phosphorylation of these sites may play a role in ARMS. Thus, these new antibodies may be used in studying the regulation of nerve and muscle development and differentiation and in finding therapeutic solutions for certain disorders, including Waardenburg syndrome and childhood solid muscle tumor alveolar rhabdomyosarcoma (ARMS).

11 Claims, 19 Drawing Sheets

OTHER PUBLICATIONS

Tajbakhsh, S. et al., "The birth of muscle progenitor cells in the mouse: spatiotemporal considerations," *Current topics in developmental biology*, vol. 48, pp. 225-268 (2000).

Williams, B.A. et al., "Pax-3 expression in segmental mesoderm marks early stages in myogenic cell specification," *Development* (Cambridge, England), vol. 120, pp. 785-796 (1994).

Xia, S.J. et al., "Chromosome translocations in sarcomas and the emergence of oncogenic transcription factors," *Eur J Cancer*, vol. 41, pp. 2513-2527 (2005).

Amstutz, R., et al., "Phosphorylation regulates transcriptional activity of PAX3/FKHR and reveals novel therapeutic possibilities," Cancer Res, vol. 68: pp. 3767-3776 (2008).

* cited by examiner

MATLAGAVPRMMRPGPGQNYPRSGFPLEVSTPLGQGRVNQLGGVFINGRPLPN
HIRHKIVEMAHHGIRPCVISRQLRVSHGCVSKILCRYQETGSIRPGAIGGSKPKQV
TTPDVEKKIEEYKRENPGMFSWEIRDKLLKDAVCDRNTVPSVSSISRILRSKFGKG
EEEEADLERKEAEESEKKAKHSIDGILSERASAPQSDEGSDIDSEPDLPLKRKQR
RSRTTFTAEQLEELERAFERTHYPDIYTREELAQRAKLTEARVQVWFSNRRARW
RKQAGANQLMAFNHLIPGGFPPTAMPTLPTYQLSEHSYQPTSIPQAVSDPSSTVH
RPQPLPPSTVHQSTIPSNADSSSAYCLPSTRHGFSSYTDSFVPPSGPSNPMNPTI
GNGLSPQVMGLLTNHGGVPHQPQTDYALSPLTGGLEPTTTVSASCSQRLEHMK
NVDSLPTSQPYCPPTYSTAGYSMDPVTGYQYGQYGQSAFHYLKPDIA

SEQ ID NO: 1

Fig. 1

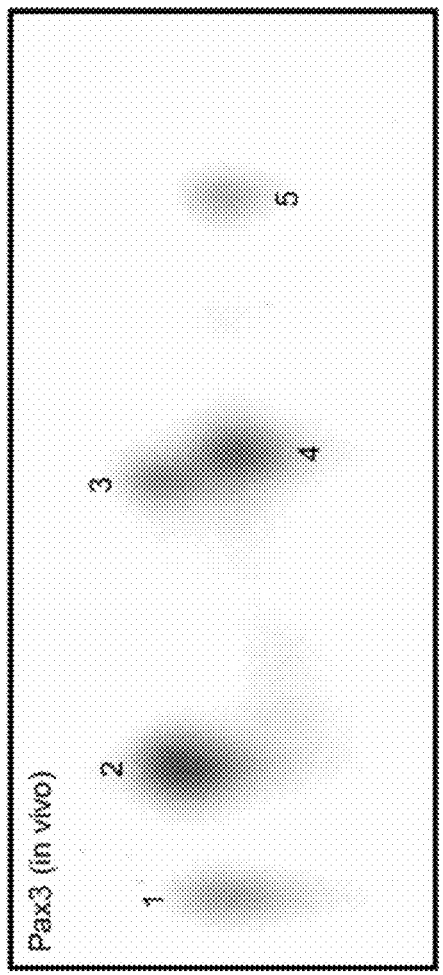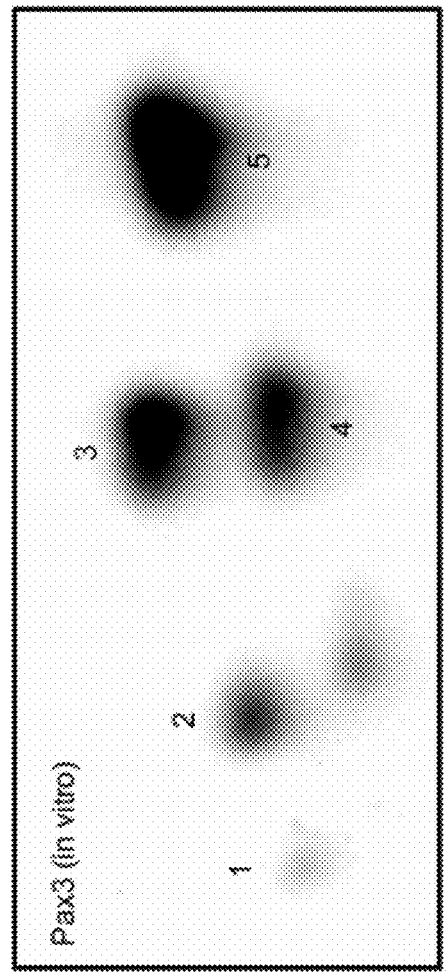

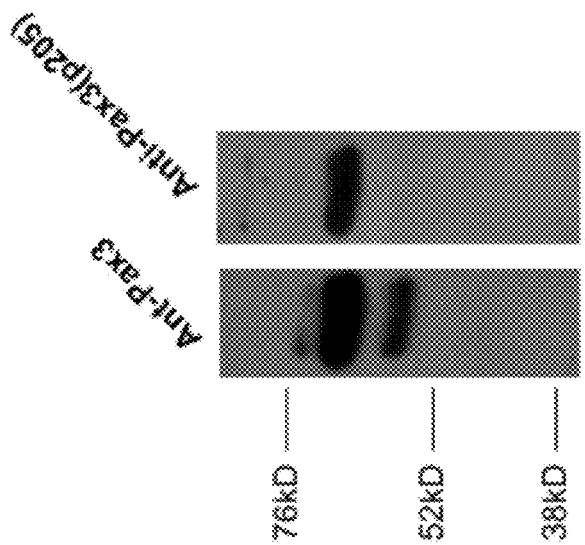
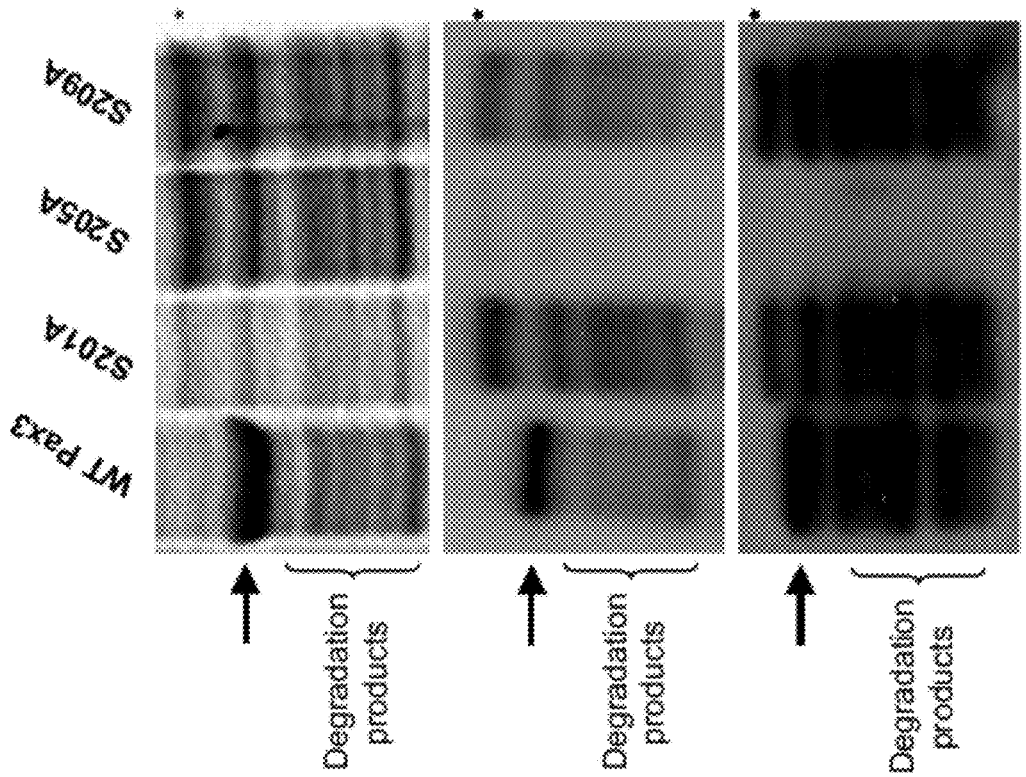
Fig. 9A
Fig. 9B

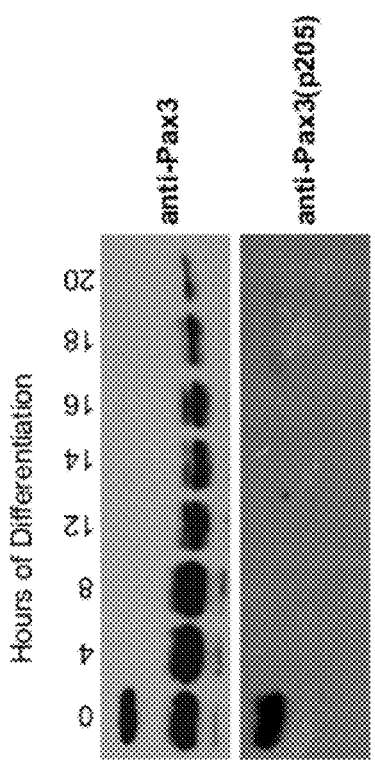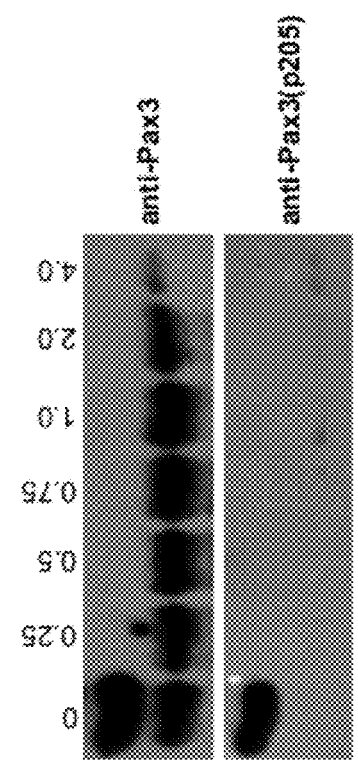

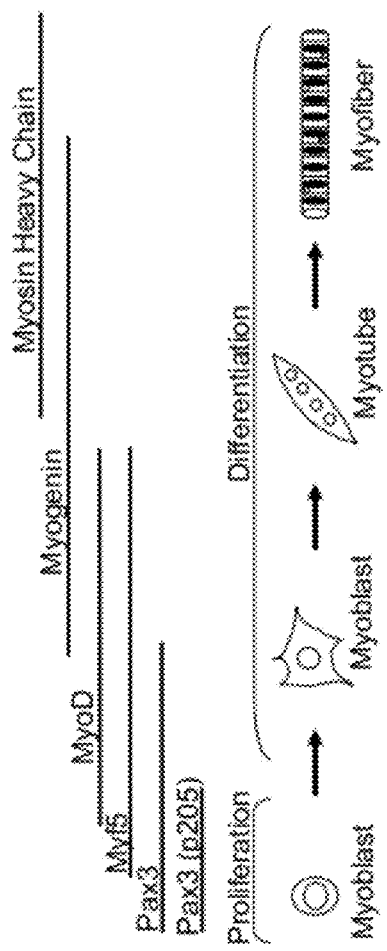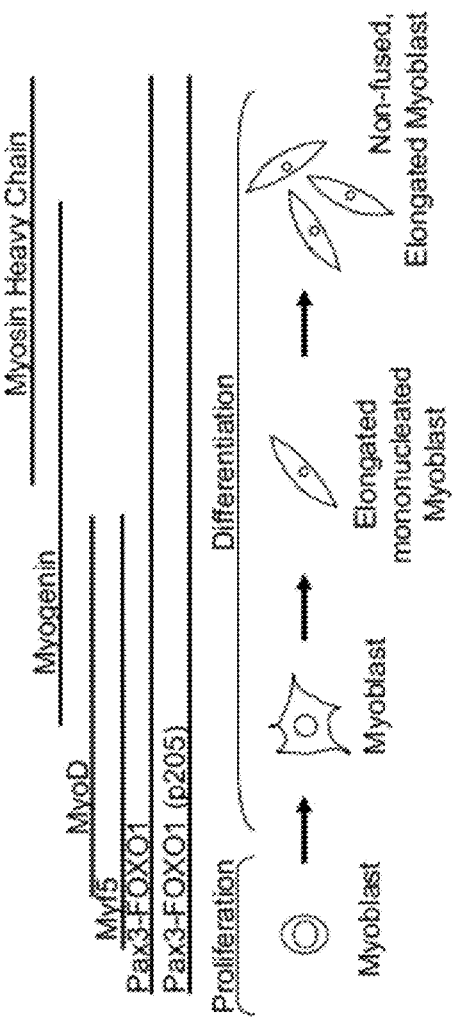
Fig. 11A
Fig. 11B

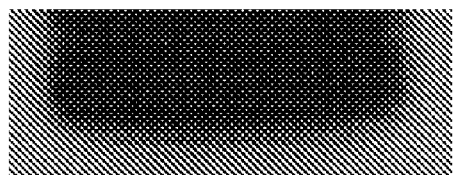 
Fig. 19

SEQUENCE LISTING

<160> NUMBER OF SEQ ID NOS: 5

<210> SEQ ID NO 1
<211> LENGTH: 484
<212> TYPE: PRT
<213> ORGANISM: Homo sapiens

<400> SEQUENCE: 1

Met Ala Thr Leu Ala Gly Ala Val Pro Arg Met Met Arg Pro Gly Pro
1               5                   10                  15

Gly Gln Asn Tyr Pro Arg Ser Gly Phe Pro Leu Glu Val Ser Thr Pro
            20                  25                  30

Leu Gly Gln Gly Arg Val Asn Gln Leu Gly Gly Val Phe Ile Asn Gly
        35                  40                  45

Arg Pro Leu Pro Asn His Ile Arg His Lys Ile Val Glu Met Ala His
50                  55                  60

His Gly Ile Arg Pro Cys Val Ile Ser Arg Gln Leu Arg Val Ser His
65                  70                  75                  80

Gly Cys Val Ser Lys Ile Leu Cys Arg Tyr Gln Glu Thr Gly Ser Ile
                85                  90                  95

Arg Pro Gly Ala Ile Gly Gly Ser Lys Pro Lys Gln Val Thr Thr Pro
            100                 105                 110

Asp Val Glu Lys Lys Ile Glu Glu Tyr Lys Arg Glu Asn Pro Gly Met
        115                 120                 125

Phe Ser Trp Glu Ile Arg Asp Lys Leu Leu Lys Asp Ala Val Cys Asp
130                 135                 140

Arg Asn Thr Val Pro Ser Val Ser Ser Ile Ser Arg Ile Leu Arg Ser
145                 150                 155                 160

Lys Phe Gly Lys Gly Glu Glu Glu Ala Asp Leu Glu Arg Lys Glu
                165                 170                 175

Ala Glu Glu Ser Glu Lys Lys Ala Lys His Ser Ile Asp Gly Ile Leu
            180                 185                 190

Ser Glu Arg Ala Ser Ala Pro Gln Ser Asp Gly Ser Asp Ile Asp
        195                 200                 205

Ser Glu Pro Asp Leu Pro Leu Lys Arg Lys Gln Arg Arg Ser Arg Thr
210                 215                 220

Thr Phe Thr Ala Glu Gln Leu Glu Glu Leu Glu Arg Ala Phe Glu Arg
225                 230                 235                 240

Thr His Tyr Pro Asp Ile Tyr Thr Arg Glu Glu Leu Ala Gln Arg Ala
                245                 250                 255

Lys Leu Thr Glu Ala Arg Val Gln Val Trp Phe Ser Asn Arg Arg Ala
            260                 265                 270

Arg Trp Arg Lys Gln Ala Gly Ala Asn Gln Leu Met Ala Phe Asn His
        275                 280                 285

Leu Ile Pro Gly Gly Phe Pro Pro Thr Ala Met Pro Thr Leu Pro Thr
290                 295                 300

Tyr Gln Leu Ser Glu His Ser Tyr Gln Pro Thr Ser Ile Pro Gln Ala
305                 310                 315                 320

Val Ser Asp Pro Ser Ser Thr Val His Arg Pro Gln Pro Leu Pro Pro
                325                 330                 335

Ser Thr Val His Gln Ser Thr Ile Pro Ser Asn Ala Asp Ser Ser Ser
            340                 345                 350

Ala Tyr Cys Leu Pro Ser Thr Arg His Gly Phe Ser Ser Tyr Thr Asp
        355                 360                 365

```
Ser Phe Val Pro Pro Ser Gly Pro Ser Asn Pro Met Asn Pro Thr Ile
    370                 375                 380

Gly Asn Gly Leu Ser Pro Gln Val Met Gly Leu Leu Thr Asn His Gly
385                 390                 395                 400

Gly Val Pro His Gln Pro Gln Thr Asp Tyr Ala Leu Ser Pro Leu Thr
                405                 410                 415

Gly Gly Leu Glu Pro Thr Thr Thr Val Ser Ala Ser Cys Ser Gln Arg
            420                 425                 430

Leu Glu His Met Lys Asn Val Asp Ser Leu Pro Thr Ser Gln Pro Tyr
        435                 440                 445

Cys Pro Pro Thr Tyr Ser Thr Ala Gly Tyr Ser Met Asp Pro Val Thr
    450                 455                 460

Gly Tyr Gln Tyr Gly Gln Tyr Gly Gln Ser Ala Phe His Tyr Leu Lys
465                 470                 475                 480

Pro Asp Ile Ala

<210> SEQ ID NO 2
<211> LENGTH: 50
<212> TYPE: PRT
<213> ORGANISM: Homo sapiens

<400> SEQUENCE: 2

Ala Glu Glu Ser Glu Lys Lys Ala Lys His Ser Ile Asp Asp Gly Ile
1               5                   10                  15

Leu Ser Glu Arg Ala Ser Ala Pro Gln Ser Asp Glu Gly Ser Asp Ile
            20                  25                  30

Asp Ser Glu Pro Asp Leu Pro Leu Lys Arg Lys Gln Arg Arg Ser Arg
        35                  40                  45

Thr Thr
    50

<210> SEQ ID NO 3
<211> LENGTH: 15
<212> TYPE: PRT
<213> ORGANISM: Artificial sequence
<220> FEATURE:
<223> OTHER INFORMATION: Synthetic

<400> SEQUENCE: 3

Cys Ala Pro Gln Ser Asp Glu Gly Ser Asp Ile Asp Ser Glu Pro
1               5                   10                  15

<210> SEQ ID NO 4
<211> LENGTH: 18
<212> TYPE: PRT
<213> ORGANISM: Artificial sequence
<220> FEATURE:
<223> OTHER INFORMATION: Synthetic

<400> SEQUENCE: 4

Cys Glu Arg Ala Ser Ala Pro Gln Ser Asp Glu Gly Ser Asp Ile Asp
1               5                   10                  15

Ser Glu

<210> SEQ ID NO 5
<211> LENGTH: 16
<212> TYPE: PRT
<213> ORGANISM: Artificial sequence
<220> FEATURE:
<223> OTHER INFORMATION: Synthetic
```

```
-continued

<400> SEQUENCE: 5

Ser Asp Glu Gly Ser Asp Ile Asp Ser Glu Pro Asp Leu Pro Leu Cys
1               5                   10                  15
```

PHOSPHO-SPECIFIC ANTI-PAX3 ANTIBODIES

The benefit of the filing date of U.S. provisional application Ser. No. 61/058,388, filed Jun. 3, 2008, is claimed under 35 U.S.C. §119(e).

This invention was partially made with United States government support under contract No. 1 P20 RR0201 52-01 awarded by the National Institutes of Health. The government has certain rights in this invention.

This invention relates to new site-specific antibodies that recognize three previously unknown sites of phosphorylation on the myogenic transcription factor, paired box 3 (Pax3), when the sites are phosphorylated. The new antibodies will be useful in studying the regulation of nerve and muscle development and differentiation, in assaying for the phosphorylated protein in biological samples, and in finding therapeutic solutions for Waardenburg syndrome and childhood solid muscle tumor alveolar rhabdomyosarcoma (ARMS).

Physiological Importance of Phosphorylation. Phosphorylation is one of several post-translational mechanisms by which the biological activity of transcription factors can be regulated. In the absence of phospho-specific antibodies, in vivo analysis of phosphorylation requires the use of large amounts of radioactivity for the metabolic labeling of the cells followed by extensive manipulation of the resulting radioactive total cell extracts. The resulting radioactive phospho-analysis cannot differentiate different sites on the same protein, nor can it identify the exact site of phosphorylation on the protein. Antibodies that can recognize a phosphorylation event at a specific amino acid negate the need for large amounts of radioactivity and allow the researcher to very easily follow the status of phosphorylation at a specific amino acid throughout various biological processes.

Pax3. Paired box 3 (Pax3) is a developmentally regulated transcription factor that is a member of the paired class homeodomain family of transcription factor proteins. Pax3 contains two distinct DNA-binding regions—the paired domain and the homeodomain; at least three distinct protein-protein interaction domains that mediate the interaction of Pax3 with regulatory proteins; and a transcriptional activation domain. The 484 amino acid sequence (SEQ ID NO:1) of human Pax3 protein is shown in FIG. 1. Pax3 is expressed in several developing tissues, including tissues associated with the central nervous system, craniofacial tissue, trunk neural crest, somites and skeletal muscle.

Pax3 plays an essential role in early skeletal muscle development. Pax3 is expressed 8.5-15 days post-conception in the neural tube, dermomyotome, and migratory population of myogenic precursors entering the developing limb bud. Expression of Pax3 precedes migration of the cells from the dermomyotome into the limb bud. The expression of Pax3 is believed to induce migration. Pax3 expression decreases once the migrating cells reach the limb bud. Pax3 is required for the formation of muscles of the trunk and for the delamination and migration of myogenic progenitor cells to the limb buds (Williams and Ordahl 1994; Tajbakhsh and Buckingham 2000; Buckingham and Relaix 2007). Pax3-deficient Splotch mice are embryonic lethal due to defects in skeletal muscle (Xia and Barr 2005), and human patients with PAX3 haploinsufficiency display limb muscle hypoplasia (Epstein et al. 1996). Pax3 is important for muscle differentiation—it is one of the initial transcription factors responsible for initiating the expression of genes required for the differentiation, i.e., the myogenic regulatory factors of MyoD, Myf-5, and myogenin (Maroto et al. 1997). It was shown that both MyoD and myogenin, two early myogenic transcription factors, are phosphorylated in proliferating myoblasts (Li et al. 1992; Kitzmann et al. 1999). Phosphorylation of these two factors inhibits their transcriptional activity, either through inhibition of DNA-binding (Li et al. 1992) or by promoting their degradation (Kitzmann et al. 1999). The phosphorylation of MyoD and myogenin is subsequently decreased upon the induction of myogenic differentiation resulting in activation of their transcriptional activity (Li et al. 1992; Kitzmann et al. 1999).

Because of the importance of Pax3 in early muscle and nerve development and in the expression of early myogenic genes, it is critical that the expression and activity of Pax3 be tightly regulated throughout differentiation. Recently, it was determined that the stability of Pax3 is regulated on a post-translational level during myogenic differentiation. Pax3 protein levels decrease significantly in the first twenty-four hours of myogenic differentiation, and this change in protein levels is regulated post-translationally since changes in mRNA levels and protein translation for Pax3 do not correlate with the decrease in Pax3 protein levels (Miller and Hollenbach 2007). Furthermore, it has been shown that Pax3 stability is regulated, in part, using the ubiquitin-proteasome system (Boutet et al. 2007).

In addition to the ubiquitin-proteasome system, it has been suggested that phosphorylation may also be important in the regulation of Pax3 biological activities (Boutet et al. 2007; Miller and Hollenbach 2007). Phosphorylation has been widely studied due to its various roles in transcription factor regulation (Hunter and Karin 1992).

Pax3 and Disorders. Pax3 is implicated in neural crest disorders, including Waardenburg syndrome. It also is a key factor in the childhood solid muscle tumor alveolar rhabdomyosarcoma (ARMS). Rhabdomyosarcoma, as a class of tumors, is the most frequent soft tissue sarcoma in children (5-8% of pediatric tumors) and consists of two main subtypes—embryonal (ERMS) and alveolar (ARMS). ARMS is the more aggressive subtype, occurs mostly in the trunk and extremities, and is believed to arise predominantly from committed skeletal muscle precursors (Buckingham and Relaix 2007). ARMS is characterized by the t(2; 13) chromosomal translocation, which results in the fusion of Pax3 to the fork head transcription factor FKHR, also called FOXO1 (FOXO1a), as illustrated in FIG. 2. The new fusion PAX3-FOXO1 protein retains the ability to bind DNA in the same sites as Pax3, but has been shown to have greater transcriptional activation than Pax3. It was recently demonstrated that a kinase inhibitor decreased the transcription activity of PAX3/FKHR, and that this inhibition occurred due to prevention of phosphorylation of more than one serine site in the PAX3 domain. Six potential serine sites were identified as potential sites, including S187, S192, S197, S201, S205, and S209, and four of these sites (S187, S201, S205, and S209) were shown to be conserved in Pax3 proteins from different species. In addition, phosphorylation of more than one serine was found to be required for DNA binding and subsequently transcriptional activity of Pax3. However, these results only indicated the region of Pax3 that was phosphorylated and did not identify the exact sites of phosphorylation (Amstutz et al. 2008).

The altered DNA binding and transcriptional activities along with the aberrant phosphorylation and increased protein stability associated with Pax3-FOXO1 are believed to contribute to the inhibition of normal myogenesis observed in ARMS tumor cells. During normal myogenesis, proliferating myoblasts exit from the cell cycle, flatten and elongate, fuse to form multinucleated myotubes, and ultimately multinucleated myofibers. The temporal expression of the muscle determination factors MyoD, Myf5, and myogenin control the progression through myogenesis with terminal differentiation being marked by the expression of myosin heavy chain. The temporal expression of Pax3, along with MyoD, Myf5, myogenin, and myosin heavy chain are shown in FIG. 11A. Pax3 has been demonstrated to be one of the earliest factors in the myogenic program by activating the expression of MyoD and perpetuating the expression of Myf5.

The aberrant expression and phosphorylation of the Pax3-FOXO1 fusion protein in the later stages of myogenesis inhibits the ability of myoblasts to fuse into multinucleated myotubes. However, Pax3-FOXO1 does not alter the temporal expression of the muscle determination factors Myf5, MyoD, myogenin, and myosin heavy chain. The temporal expression of Pax3-FOXO1, MyoD, Myf5, myogenin, and myosin heavy chain are shown in FIG. 11B.

We have shown that Pax3, a member of the paired class homeodomain family of transcription factors and an essential protein for early neural and skeletal muscle development, is indeed phosphorylated in proliferating mouse primary myoblasts. Furthermore, we have identified Ser205 as one of the three sites of phosphorylation on Pax3 in proliferating mouse primary myoblasts. We have also shown that the phosphorylation status of Pax3 changes rapidly upon the induction of myogenic differentiation. We have identified Ser201 and Ser209 as additional sites of Pax3 phosphorylation in vitro, and determined that these sites are also used in vivo in proliferating primary myoblasts. The phosphorylation of Ser205 was shown to be required for the efficient phosphorylation of Ser201 or Ser209, and was shown to enhance DNA binding. These three sites are also present in the Pax3-FOXO1 fusion protein. We have also shown that this fusion protein is phosphorylated in vivo, and that the phosphorylation is at Ser205. The timing of expression of Pax3 and Pax3-FOXO1 and the pattern of phosphorylation were shown to be quite different during myogenic differentiation. The phosphorylation of Pax3-FOXO1 at these serine sites may play a role in ARMS and other changes due to the lasting presence of this fusion protein. In addition, site-specific antibodies were made to each of these three sites (Ser201, Ser205, and Ser209) when phosphorylated. These antibodies will be useful in studying the regulation of nerve and muscle development and differentiation and the transcription activity of Pax3, and in finding therapeutic solutions for disorders, including Waardenburg syndrome and childhood solid muscle tumor alveolar rhabdomyosarcoma (ARMS).

BRIEF DESCRIPTION OF THE DRAWINGS

FIG. 1 illustrates the amino acid sequence of Pax3 peptide (SEQ ID NO:1). The three identified sites of phosphorylation are indicated by the large, bold, underlined letters and are in order: Ser201, Ser205, and Ser209.

FIGS. 5A and 5B illustrate the development of an in vitro kinase assay to facilitate the identification of phosphorylation sites on Pax3. FIG. 5A illustrates that proliferating mouse primary myoblasts stably expressing FLAG-Pax3 were metabolically labeled with [$^{32}$P]-orthophosphate and FLAG-Pax3 was immunoprecipitated from total cell extracts using an anti-FLAG antibody. The resulting radiolabeled protein was isolated from the dried 12% SDS-PAGE gel and subjected to two-dimensional phosphopeptide analysis. FIG. 5B illustrates the results of bacterially expressed and purified GST-Pax3 that was phosphorylated using the in vitro kinase assay. The radiolabeled protein was isolated from the dried 10% SDS-PAGE gel and subjected to two-dimensional phosphopeptide analysis. In both FIGS. 5A and 5B the five distinctly migrating phosphopeptides are indicated by numbers one through five.

FIG. 7A shows a schematic of the primary amino acid sequence of the region deleted in the ΔPDOD mutant (SEQ ID NO. 2). The octapeptide domain (OD) is indicated by the bracket and the eight serines present in this region are underlined. The smaller bold arrows indicate the predicted minor sites of trypsin cleavage, and the larger bold arrows indicate the predicted major sites of cleavage. FIG. 7B shows the bacterially expressed and purified GST-Pax3 and the individual GST-Pax3 phospho-incompetent mutants that were separated by 8% SDS-PAGE and visualized by Coomassie staining. FIG. 7C shows the same GST proteins as in FIG. 7B that were used in parallel in vitro kinase assays, separated by 8% SDS-PAGE, and visualized by autoradiography. In FIGS. 7B and 7C, the mobilities of the wild-type Pax3 and the Pax3 point mutants are indicated by the arrows. Wildtype Pax3 lacks the carboxyl terminus, which was demonstrated not to affect phosphorylation, and therefore migrates with a slightly faster mobility.

FIGS. 9A and 9B illustrate results of experiments that confirm the phosphorylation of serine 205 in vivo. FIG. 9A shows results of using equal amounts of bacterially expressed and purified GST-Pax3 and three GST-Pax3 phospho-incompetent point mutants in independent in vitro kinase assays using [γ-$^{32}$P]-ATP to confirm phosphorylation or with cold ATP. The proteins that were non-radioactively labeled were subsequently used for Western blot analysis using an antibody that was raised against a synthetic protein specifically phosphorylated at serine 205, the anti-Pax3(p205). The top panel shows the results of Coomassie staining to demonstrate equal amounts of protein; the middle panel shows the results of independent radiolabeling to confirm the phosphorylation status; and the bottom panel shows the results of Western blot analysis using the anti-Pax3(p205) antibody. The arrow in each panel indicates the mobility of wildtype Pax3, and the asterisk indicates the mobility of the phospho-incompetent point mutants. FIG. 9B shows that Pax3 is phosphorylated at Ser205 in proliferating mouse primary myoblasts. Total cell extract was isolated from proliferating mouse primary myoblasts, and a Western blot analysis was performed on 50 μg of total cell extract using either the general anti-Pax3 antibody (left panel) or anti-Pax3(p205) antibody (right panel).

FIGS. 10A and 10B show that phosphorylation of Pax3 at serine 205 is rapidly abolished upon the induction of differentiation. Proliferating mouse primary myoblasts were induced to differentiate for 0-20 hours (FIG. 10A) or for 0-4 hours (FIG. 10B). Total cell extracts were created from the differentiated myoblasts at the indicated time points and a standard Western blot analysis was performed on 50 μg of total cell extract using the anti-Pax3 antibody (top panels) or the anti-Pax3(p205) antibody (bottom panels).

FIGS. 11A and 11B are schematics of normal myogenesis (FIG. 11A) and myogenesis in the presence of Pax3-FOXO1 (FIG. 11B). The temporal expression of Pax3, Pax3(p205), Pax3-FOXO1, Pax3-FOXO1 (p205), MyoD, Myf5, myogenin, and myosin heavy chain are indicated by the lines above the diagram.

FIG. 19 illustrates the results of Western blot analysis showing phosphorylation of endogenous Pax3-FOXO1 at Ser205 in the ARMS tumor cell line RH30.

Figure 2:
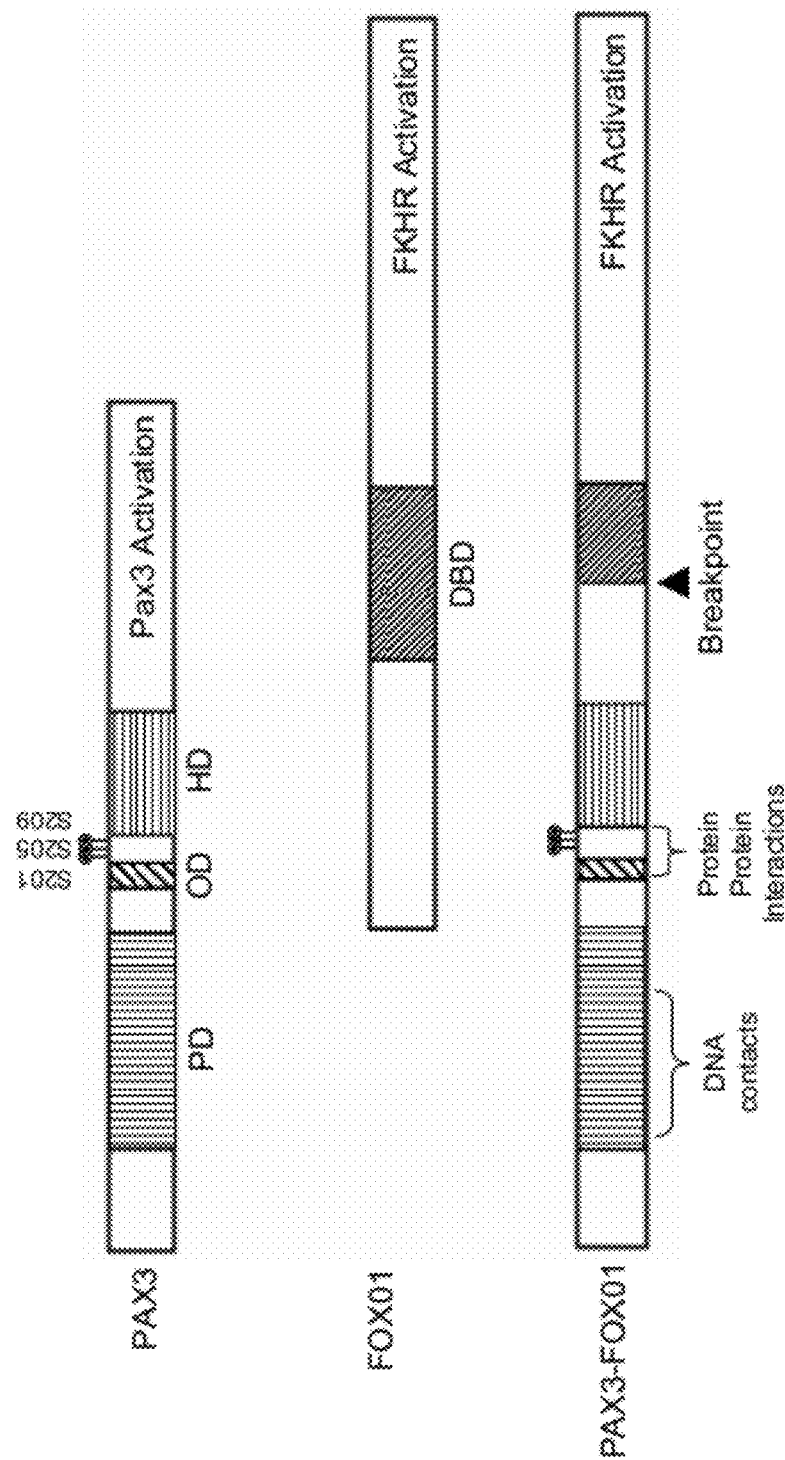
FIG. 2 is a schematic of the PAX3 protein, the FOXO1 protein, and the PAX3-FOXO1 fusion protein. Abbreviations used in FIG. 2 are the following: PD=Paired DNA binding domain; OD=Octapeptide Domain; HD=Homeodomain DNA binding domain; DBD=DNA Binding Domain.

We have found the first evidence that Pax3 exists as a phosphoprotein in proliferating mouse primary myoblasts. Using an in vitro kinase assay, deletion, and point mutant analysis, we conclusively identified Ser205, Ser201, and Ser209 as the only sites of phosphorylation on Pax3. The phosphorylation of Ser205 on endogenously expressed Pax3 was confirmed in vivo using antibodies specific for phosphorylation at Ser205. Site-specific antibodies have been made to phosphor-Ser201, phosphor-Ser205, and phosphor-Ser209. Bacterially expressed GST-Pax3 or the indicated Pax3 point mutants were phosphorylated using our in vitro kinase assay and confirmed by parallel radioactivity assays. Proteins were separated and the serum from the indicated rabbit was tested by Western blot analysis, and the antibodies were shown to be site specific. These three sites of phosphorylation are also present in the Pax3-FOXO1 fusion protein. We have also shown that this fusion protein is phosphorylated in vivo, and that the phosphorylation is at Ser205. The timing of expression of Pax3 and Pax3-FOXO1 and the pattern of phosphorylation were shown to be quite different during myogenic differentiation. The phosphorylation of Pax3-FOXO1 at these serine sites may play a role in ARMS and other changes due to the lasting presence of this fusion protein.

We have shown for the first time that the phosphorylation status of endogenous Pax3 and Pax3-FOXO1 shows a different pattern on the induction of myogenic differentiation. The presence of phosphorylation in a region of Pax3 important for mediating protein-protein interactions and the fact that phosphorylation is lost upon induction of differentiation indicates that the phosphorylation of Pax3 is biologically relevant during differentiation. These new site-specific antibodies can be used to monitor cellular localization of phosphorylated Pax3 or phosphorylated Pax3-FOXO1, to monitor the temporal expression of the phosphorylated protein during development, to aid in immunoprecipitation of specifically phosphorylated protein, to monitor the effect of kinase inhibitors on the phosphorylation of Pax3 or Pax3-FOXO1, to facilitate the identification of therapeutic drugs by monitoring the ability of novel molecular compounds specific for a particular kinase to specifically inhibit phosphorylation of Pax3 or Pax3-FOXO1 at a specific site, to monitor the phosphorylation status of Pax3-FOXO1 in tumor samples, and to monitor phosphorylation status in animal models or tumor models to monitor the effects of novel drugs on the phosphorylation status of Pax3 or Pax3-FOXO1.

DEFINITIONS

The term "antibody" herein used is intended to include intact antibodies, such as polyclonal antibodies or monoclonal antibodies, as well as proteolytic fragments thereof, such as the Fab or F(ab')2 fragments. Further, the term "antibody" is intended to include the variable portion of the heavy and/or light chains of the intact antibody, and chimeric or single-chain antibodies incorporating such reactive fractions, or molecules developed to deliver therapeutic moieties by means of a portion of the molecule which contained a reactive fraction. Such molecules may be provided by any known technique, including, but not limited to, enzymatic cleavage, peptide synthesis, or recombinant techniques. The term "antigen-binding fragment" is used to include fragments of the antibody that still bind the phosphorylated protein Pax3. The term "epitope" herein used is meant to refer to that portion of any molecule capable of being bound by an antibody which can also be recognized by that antibody. The term "polyclonal antibody" herein used is meant to refer to antibodies which are heterogeneous populations derived from the sera of animals immunized with an antigen and which are shown to bind to the specific antigen. The term "monoclonal antibody" herein used is meant to refer to antibodies which are a substantially homogeneous population of an antibody to a specific antigen. The term "phospho-specific antibody" herein used means a specific antibody against the phosphorylated amino acid residue. A phospho-specific antibody does not detect un-phosphorylated residues.

The term "Pax3" refers to the translated paired box 3 protein, and is meant to include any post-translation modification to that protein. The sequence of Pax3 is shown in FIG. 1 (SEQ ID NO.1). As written the term "PAX3" refers to the gene that encodes for Pax3. The present invention discloses three phospho-specific antibodies against sites in Pax3 which include, anti-phospho-serine 201 Pax3 Antibody (Anti-p201 Pax3), anti-phospho-serine 205 Pax3 Antibody (Anti-p205 Pax3); and anti-phospho-serine 209 Pax3 Antibody (Anti-p209 Pax3).

EXAMPLE 1

Materials and Methods

Cell culture conditions. Mouse primary myoblasts were isolated from 2-4 day-old C57/B16 mice as previously described (Rando and Blau 1997; Miller and Hollenbach 2007). Proliferation medium for the mouse primary myoblasts consisted of Ham's F-10 nutrient medium (Mediatech Cellgro, Herndon, Va.) supplemented with 20% Fetal Bovine Serum (FBS) (HyClone Laboratories, Inc., Logan, Utah), 2.5 ng/ml bFGF (Promega Corp., Madison, Wis.), 15 mM HEPES and Penicillin-Streptomycin. Differentiation medium consisted of Dulbecco's Modified Eagle's Medium (DMEM, GIBCO® BRL), supplemented with 2% horse serum (HyClone). All media contained penicillin G (200 U/ml) and streptomycin (200 g/ml) (Mediatech Corp., Herndon, Va.). DMEM was additionally supplemented with L-glutamine (2 mM, GIBCO® BRL) and when prepared in this manner referred to as DMEM-complete. Cells were grown in a humidified incubator at 37° C. in 5% $CO_2$. All cells were grown on collagen-coated dishes (Becton Dickinson Labware, Bedford, Mass.), were passage-matched to prevent possible differences due to different passage conditions, were not used past passage 9 to prevent the cells entering crisis, and were not allowed to grow past approximately 80% confluency to maintain the cells in an undifferentiated state. To induce the differentiation of primary myoblasts, the proliferation media was removed, the cells were washed twice with phosphate buffer saline (PBS), the media were replaced with 10 ml of differentiation media, and the cells were grown as described above until needed for further analysis.

Retroviral stocks and the stable transduction of mouse primary myoblasts. Retroviral stocks were generated by transient transfection by the Fugene™ method (Roche Applied Science, Indianapolis, Ind.) of the ecotropic Phoenix packaging cell line (as described by Swift et al. 1999) with 8 μg of the MSCV-IRES-GFP retroviral construct (described below) containing either a FLAG-epitope tagged Pax3 (FLAG-Pax3) or FLAG-Pax3(S205A) in which serine 205 has been mutated to an alanine. Culture supernatants containing virus were collected between 36 and 72 hours after transfection, filtered, and subsequently used for a single transduction of mouse primary myoblasts. Three to seven days post-transduction, primary myoblasts were harvested in F10 media supplemented with collagen (10 ng/ml) (Sigma, St. Louis, Mo.) and cells expressing GFP were selected by fluorescence-activated cell sorting (FACS) analysis. Cells selected in this manner were cultured and expanded as described above.

Creation of expression constructs. The retroviral constructs MSCV-FLAG-Pax3-IRES-GFP and FLAG-Pax3 (S205A), and the GST-fusion constructs pGEX-5X-1-Pax3 and its corresponding domain deletion mutants were obtained from St. Jude Children's Research Hospital (Memphis, Tenn.). The MSCV-FLAG-IRES-GFP constructs contained either the cDNA for Pax3 or for Pax3 in which serine 205 had been mutated to an alanine with a FLAG-epitope tag engineered onto its amino terminus. They also contained the cDNA for the green fluorescent protein (GFP). The presence of the IRES allowed the dual production of GFP and FLAG-Pax3, both under control of the Murine Stem Cell Virus (MSCV) promoter (Laker et al. 1998).

Phospho-incompetent pGEX-5X-1-Pax3 point mutants, in which the indicated serine has been mutated to an alanine at several sites (S180A, S187A, S193A, S197A, S201A, S205A, S209A, S222A) were created using overlap extension PCR as described previously (Ho et al. 1989). The resulting PCR product was cloned into the pCRII vector using the TA Cloning Kit (Invitrogen, Carlsbad, Calif.). DNA sequencing was used to confirm the presence of the desired mutation and to confirm that no additional mutations were introduced during PCR. Following a StuI-XhoI digestion of pCRII Pax3 point mutant constructs, the inserts containing the mutation were gel extracted and ligated into the pGEX-5X-1-Pax3 parent vector, which had previously been digested with the same enzymes. The resulting wild-type and the point mutant vectors were individually transformed into Rosetta(DE3) pLysS chemically competent cells (EMD Chemicals, Gibbstown, N.J.) and subsequently used for expression and purification, as previously described (Hollenbach et al. 1999; Hollenbach et al. 2002). Bacterially expressed and purified GST-Pax3 or the GST-Pax3 deletion or point mutants were used without elution from the resin. Protein expression and purity was confirmed by SDS-PAGE analysis, and the relative protein concentrations on the resin were estimated by comparison to proteins of known concentration (data not shown).

[$^{32}$P]-Orthophosphate or [$^{35}$S]-Methionine Metabolic Labeling. Mouse primary myoblasts isolated as described above were grown to 70%-80% confluency, washed twice with filter-sterilized Tris-buffered saline (TBS), and starved of phosphates by incubating them for 30 min at 37° C. in 5% $CO_2$ with phosphate-free DMEM-complete supplemented with 2.5 ng/ml bFGF. [$^{32}$P]-Orthophosphate or [$^{35}$S]-Methionine (MP Biomedicals, Aurora, Ohio) was then added to the media (0.25 mCi/ml) and allowed to incubate for an additional 2 hours under identical conditions. After metabolic labeling, the cells were washed 3× with sterile TBS and lysed by the addition of 500 μL of lysis buffer (50 mM Tris-HCl [pH 7.4], 150 mM NaCl, 1 mM EDTA, 1% Triton X-100) containing the complete mini-protease inhibitor cocktail (Roche Applied Science), phosphatase cocktail I specific for serine/threonine phosphatases (Sigma), and phosphatase cocktail II specific for tyrosine phosphatases (Sigma) followed by incubation at room temperature with shaking for 15-30 min. Following this incubation, the lysed cells were scraped from the dish using a cell lifter, transferred to a 1.5 mL microfuge tube, and the cellular debris was removed by centrifugation at maximum speed at 4° C. for 10 minutes in an Eppendorf refrigerated microfuge. The resulting supernatant was transferred to a fresh 1.5 mL microcentrifuge tube. To immunoprecipitate the FLAG-Pax3 proteins, 40 µl anti-FLAG M2 affinity gel suspension (Sigma) was added to 1 mL of the cell lysate and the mixture was incubated with rotation for at least 2 hours at 4° C. Following this incubation, the tubes were centrifuged to pellet the resin, which was subsequently washed 3× with 500 µl TBS. SDS-PAGE loading buffer was added, the samples were boiled for 5 minutes, and the eluted proteins were separated on a 10% SDS-PAGE gel. The gel was then dried and visualized by autoradiography.

In vitro kinase assay and two-dimensional phosphopeptide analysis. GST-Pax3 or the GST-Pax3 mutants present on the resin (8 µl of resin—approximately 1 µg of protein), prepared as described above, was mixed with 26 µl of the kinase stock solution (2× kinase buffer [80 mM HEPES, 20 mM $MgCl_2$, 100 mM KCl, 2 mM DTT], 2× phosphatase inhibitor cocktails described above, 84 µM ATP, 50 µCi [-$^{32}$P]-ATP [MP Biomedicals]). The kinase reaction was initiated by the addition of 25 µl of proliferating mouse primary myoblast total cell extracts (2 µg/µl), prepared as previously described (Miller and Hollenbach 2007), and incubated for one hour at 30° C. After incubation, the beads were washed 3× with 100 µl PBS, the radiolabeled protein was eluted by boiling in 25 µl SDS-PAGE loading buffer, and separated by 10% SDS-PAGE. The resulting gels were dried and exposed to film at −80° C. overnight.

Following the in vitro kinase assay or metabolic labeling described above, the radiolabeled protein band corresponding to the phosphorylated Pax3 was extracted from the gel and submitted to two-dimensional phosphopeptide analysis as previously described (Boyle et al. 1991).

Antibodies and Western blot analysis. Quality Controlled Biomedicals (QCB—Hopkinton, Mass.) was contacted to generate a polyclonal antibody against p205 in rabbits. An antibody specific for phosphorylation of Pax3 at serine 205, anti-Pax3(p205), was produced by rabbit immunization using the following synthetic phosphopeptide: $NH_2$-CAPQSDEG (pS)DIDSEP-$CO_2$ [SEQ ID NO. 3] (QCB Custom Immunology Group). The antibody was affinity purified by QCB Custom Immunology Group, and the specificity was confirmed by Western blot analysis. Rabbits were immunized with this peptide, and were test-bled against bacterially expressed and in vitro phosphorylated Pax3 and the corresponding Pax3 Ser to Ala point mutant (the non-phosphorylatable mutant). The Pax3-specific antibody was described previously (Lam et al. 1999) and was used without further purification.

GenScript Corporation (Piscataway, N.J.) was contacted to generate polyclonal antibodies against p201 and p209 in rabbits, similar to the procedure described above. They generated phospho-peptides for each of these two phosphorylation sites. The synthetic phosphopeptides for pSer 201 and pSer209 are $NH_2$-CERASAPQ(pS)DEGSDIDSE-$CO_2$ [SEQ ID NO. 4] and $NH_2$-SDEGSDID(pS)EPDLPLC-$CO_2$ [SEQ ID NO. 5], respectively. Rabbits were individually immunized with each peptide, and we tested bleeds from these rabbits against bacterially expressed and in vitro phosphorylated Pax3 and the corresponding Pax3 Ser to Ala point mutant (the non-phosphorylatable mutant). The in vitro phosphorylation assay described above was demonstrated to mimic the in vivo phosphopeptide pattern and was used to identify the three sites of phosphorylation in vitro. Upon the confirmation of antibody specificity, the blood was collected, and the antibody was affinity purified for subsequent use.

Figure 3:
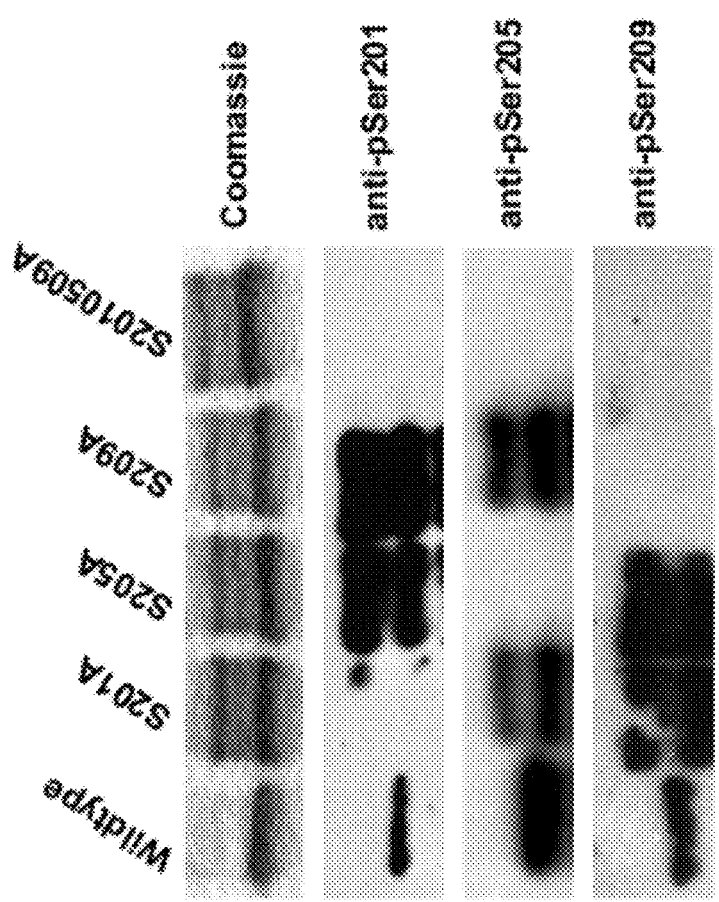
FIG. 3 illustrates the results of a Western blot analysis showing the specificity of the disclosed antibodies: anti-phospho-Ser201, anti-phospho-Ser205, and anti-phospho-Ser209, using non-phosphorylatable serine-to-alanine point mutations and wild type Pax3.

Bacterially expressed GST-Pax3 or the indicated Pax3 point mutants were phosphorylated using the in vitro kinase assay and confirmed by parallel radioactivity assays. Proteins were separated and the serum from the indicated rabbit was tested by Western blot analysis. The results are shown in FIG. 3, and indicate that all three antibodies are site-specific for a phosphorylated Pax3.

Total cell extracts from proliferating primary myoblasts or myoblasts that were induced to differentiate for a specific period of time were prepared as described above. A constant amount of total cell extract (50 µg) was separated by 10% SDS-PAGE, proteins were transferred to Immobilon-P membrane (Millipore, Bedford, Mass.), and the presence of Pax3 or Pax3 phosphorylated at serine 205 was detected using the affinity purified, monospecific Pax3 antibody or the Pax3 (p205) antibody, using previously described conditions (Lam et al. 1999).

EXAMPLE 2

Pax3 and Pax3-FOXO1 are Phosphorylated in Proliferating Primary Myoblasts

Figure 4:
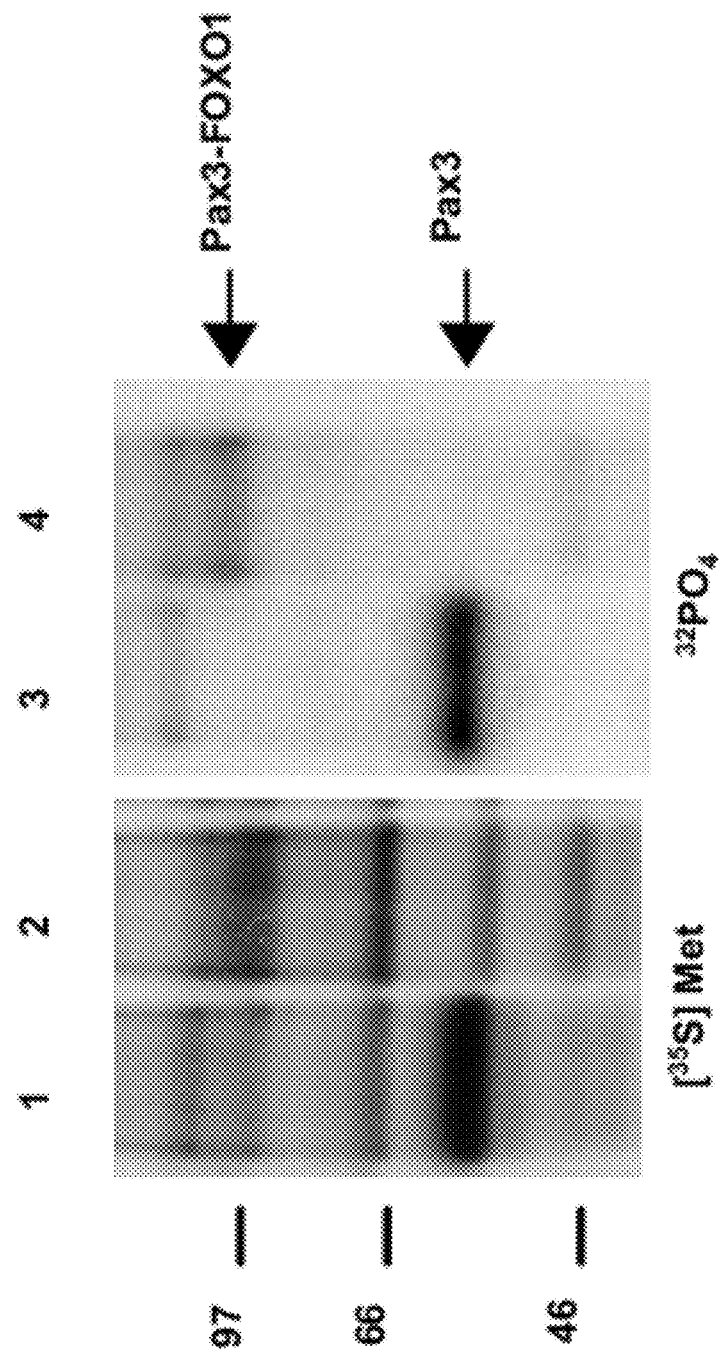
FIG. 4 illustrates that Pax3 and Pax3-FOX are phosphorylated in proliferating mouse primary myoblasts. Proliferating mouse primary myoblasts stably transduced with an amino-terminal FLAG epitope tagged Pax3 or Pax3-FOXO1 were metabolically labeled with either [$^{35}$S]-Methionine or [$^{32}$P]-orthophosphate, and FLAG-Pax3 or FLAG-Pax3-FOXO1 was immunoprecipitated from total cell extracts using an anti-FLAG antibody. The resulting immunoprecipitates were separated by 12% SDS-PAGE and the radiolabeled species were detected by autoradiography.

To define the qualitative phosphorylation status of Pax3 and Pax3-FOXO1 in proliferating primary myoblasts, isolated primary myoblasts from C57/B16 mice were isolated (as previously described above), and the primary myoblast culture was shown to be greater than 99% pure using antibodies against the myogenic markers desmin and MyoD (data not shown). Then primary myoblasts were stably transduced with a retroviral construct containing either a FLAG-epitope tagged version of Pax3 (FLAG-Pax3) or FLAG-Pax3-FOXO1 and the green fluorescent protein (GFP), and selecting the GFP expressing cells by fluorescent-activated cell sorting (FACS). Myoblasts transduced in this manner express levels of Pax3 and Pax3-FOXO1 protein that are similar to endogenous levels in primary myoblasts and the ARMS tumor cell line RH30, respectively (data not shown). The stably transduced cells were metabolically labeled with either [$^{32}$P]-orthophosphate or [$^{35}$S]-Methionine and FLAG-Pax3 or FLAG-Pax3-FOXO1 were immunoprecipitated with a FLAG-specific antibody, as described above. The results are shown in FIG. 4. The specific incorporation of both radiolabels into Pax3 and Pax3-FOXO1 was observed demonstrating that these two proteins are both expressed and phosphorylated in proliferating primary myoblasts.

This result provides the first evidence that Pax3 and Pax3-FOXO1 exist as phosphoproteins in a physiologically relevant cell type. In order to further characterize the in vivo phosphorylation of Pax3, a two-dimensional phosphopeptide map of FLAG-Pax3 that had been metabolically labeled with [$^{32}$P]-orthophosphate was generated. Proliferating mouse primary myoblasts stably expressing FLAG-Pax3 were metabolically labeled with [$^{32}$P]-orthophosphate and FLAG-Pax3 was immunoprecipitated from total cell extracts using an anti-FLAG antibody. The resulting radiolabeled protein was isolated from the dried 12% SDS-PAGE gel and subjected to two-dimensional phosphopeptide analysis, as previously described (Boyle et al. 1991). The results are shown in FIG. 5A. The phosphopeptide analysis demonstrates the presence of five distinct radiolabeled peptides, suggesting multiple sites of phosphorylation may be present (FIG. 5A).

EXAMPLE 3

Development and Validation of an In Vitro Kinase Assay

Because the generation of an in vivo phosphopeptide map required a substantial amount of [$^{32}$P]-orthophosphate and a minimum exposure period of at least six weeks, using this technique was not an efficient method of identification of the sites of phosphorylation on Pax3. In addition, several attempts at using mass spectral analysis to identify the sites of phosphorylation did not yield usable results. Therefore, to facilitate the identification of the site(s) of phosphorylation on Pax3, an in vitro kinase assay was needed that would use smaller amounts of radioactivity and require shorter exposure times expediting the analysis. Bacterially expressed and purified GST-Pax3 was phosphorylated using our in vitro kinase assay. The radiolabeled protein was isolated from the dried 10% SDS-PAGE gel and subjected to two-dimensional phosphopeptide analysis. The phosphorylated protein was analyzed by two-dimensional phosphopeptide analysis in order to verify that the in vitro phosphopeptide map of Pax3 was similar to the in vivo map. The results are shown in FIG. 5B. The in vitro method required considerably less radioactivity and required an exposure period of only 12-24 hours. The in vitro phosphopeptide map of Pax3 contained five distinct radiolabeled peptides with mobilities that are similar to that seen for the in vivo map (FIGS. 5A and 5B). Because the phosphopeptide maps of the in vitro and in vivo assays were essentially identical, the in vitro method is sufficient to perform an initial identification of the site(s) of phosphorylation on Pax3.

EXAMPLE 4

Figure 6:
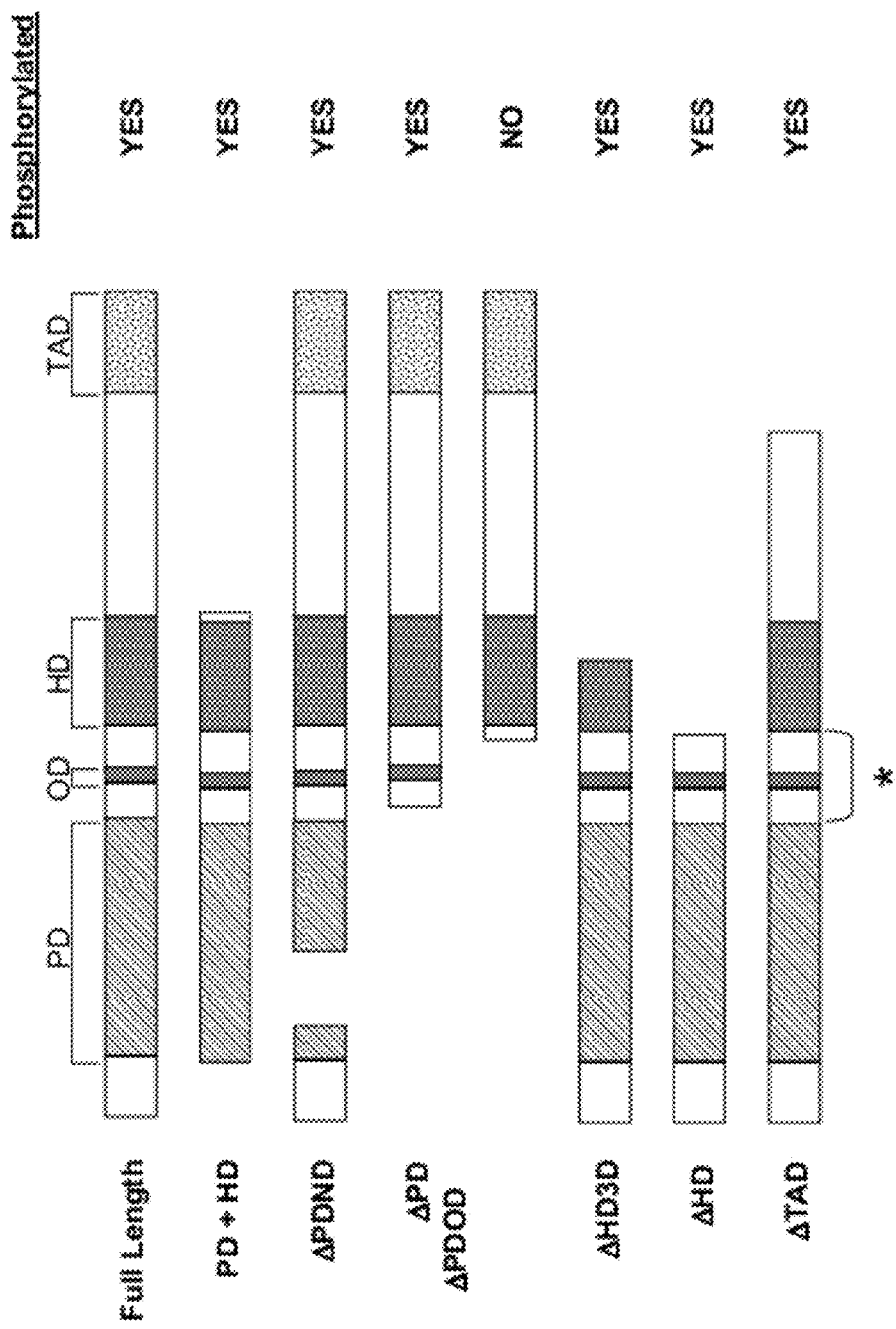
FIG. 6 illustrates the various forms of Pax3 with structural domains removed that indicated that Pax3 is phosphorylated in the region surrounding the octapeptide domain. The in vitro kinase assay was performed on bacterially expressed and purified GST-Pax3 deletion mutants that had key Pax3 structural domains removed. The overall phosphorylation status of each of the mutants is indicated. The domains of Pax3 are as follows: the paired DNA binding domain (PD), the octapeptide domain (OD), the homeodomain DNA binding domain (HD), and the transcriptional activation domain (TAD). The bracket and asterisk indicate the region of Pax3 that is phosphorylated.

Phospho-Amino Acid is Located on Region of Pax3 Surrounding the Octapeptide Domain In an effort to identify the region of Pax3 that is phosphorylated, GST-Pax3 deletion mutants were created as shown in FIG. 6 for use in the in vitro kinase assay. The deletion mutants targeted key regions of Pax3 that are required for its interaction with DNA (PDND, PD, HD3D, and HD), transcriptional activity (TAD and PD+HD), or mediating protein-protein interactions (PDOD). The overall phosphorylation status of each of the mutants is indicated if FIG. 6. The domains of Pax3 are as follows: the paired DNA binding domain (PD), the octapeptide domain (OD), the homeodomain DNA binding domain (HD), and the transcriptional activation domain (TAD). No apparent change in the phosphorylation status in most of the deletion mutants was seen in the in vitro kinase assay. Only when the region surrounding the octapeptide domain was deleted (PDOD) was a complete loss of phosphorylation observed. (FIG. 6). In FIG. 6, the bracket and asterisk indicate the region of Pax3 that is phosphorylated. This result demonstrates that the phosphorylation of Pax3 occurs primarily in the region surrounding the octapeptide domain. The three identified sites—Ser201, Ser205, and Ser209—are all close to the octapeptide domain as shown in FIG. 7A.

EXAMPLE 5

Ser205 is a Site of Pax3 Phosphorylation In Vitro

Figure 7A:
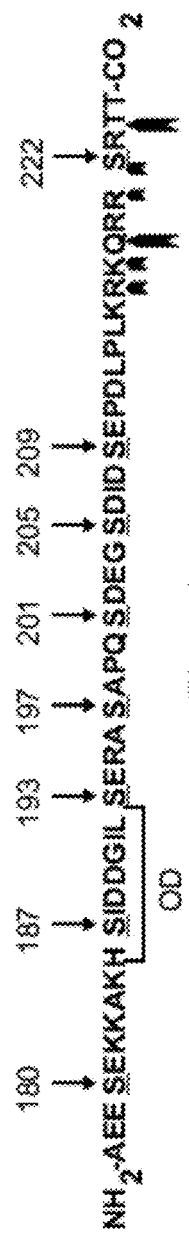
FIGS. 7A-7C indicate results showing that Pax3 is phosphorylated at serine 205 in vitro.
Figure 7B:
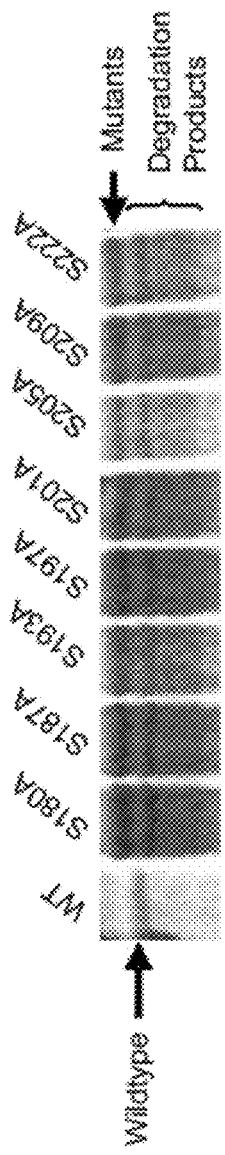
Figure 7C:
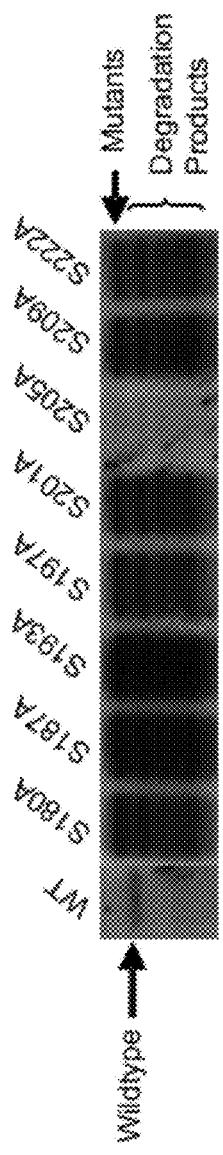

A close examination of the amino acids deleted in the PDOD mutant revealed the presence of eight serines and two threonines that could act as sites of phosphorylation (FIG. 7A). A schematic of the primary amino acid sequence of the region deleted in the PDOD mutant is shown in FIG. 7A. The octapeptide domain (OD) is indicated by the bracket and the eight serines present close to this domain are underlined. The smaller bold arrows indicate the predicted minor sites of trypsin cleavage and the larger bold arrows indicate the predicted major sites of cleavage. An independent phospho-amino acid analysis demonstrated that only serines are phosphorylated on Pax3 (data not shown). Therefore, attention was focused on the eight serines located in the region surrounding the octapeptide domain. Several phospho-incompetent GST-Pax3 point mutants were created by independently converting each serine to an alanine, and then each of these mutants were used in the in vitro kinase assay. Bacterially expressed and purified GST-Pax3 and the individual GST-Pax3 phospho-incompetent mutants were separated by 8% SDS-PAGE and visualized by Coomassie staining. The results are shown in FIG. 7B. The same GST proteins were used in parallel in vitro kinase assays, separated by 8% SDS-PAGE, and visualized by autoradiography. The results are shown in FIG. 7C. In FIGS. 7B and 7C, the mobilities of the wildtype Pax3 and the Pax3 point mutants are indicated by the arrows. Wildtype Pax3 lacks the carboxyl terminus, which was determined to not affect phosphorylation (data not shown), and therefore migrates with a slightly faster mobility. As seen with the deletion mutants, a majority of the point mutants showed no apparent change in phosphorylation despite similar levels of total protein. When serine 205 is mutated to alanine (S205A), a significant decrease in phosphorylation was observed as when compared to wildtype Pax3 (FIGS. 7B and 7C). This indicates that serine 205 is a primary site of phosphorylation on Pax3.

Figure 8:
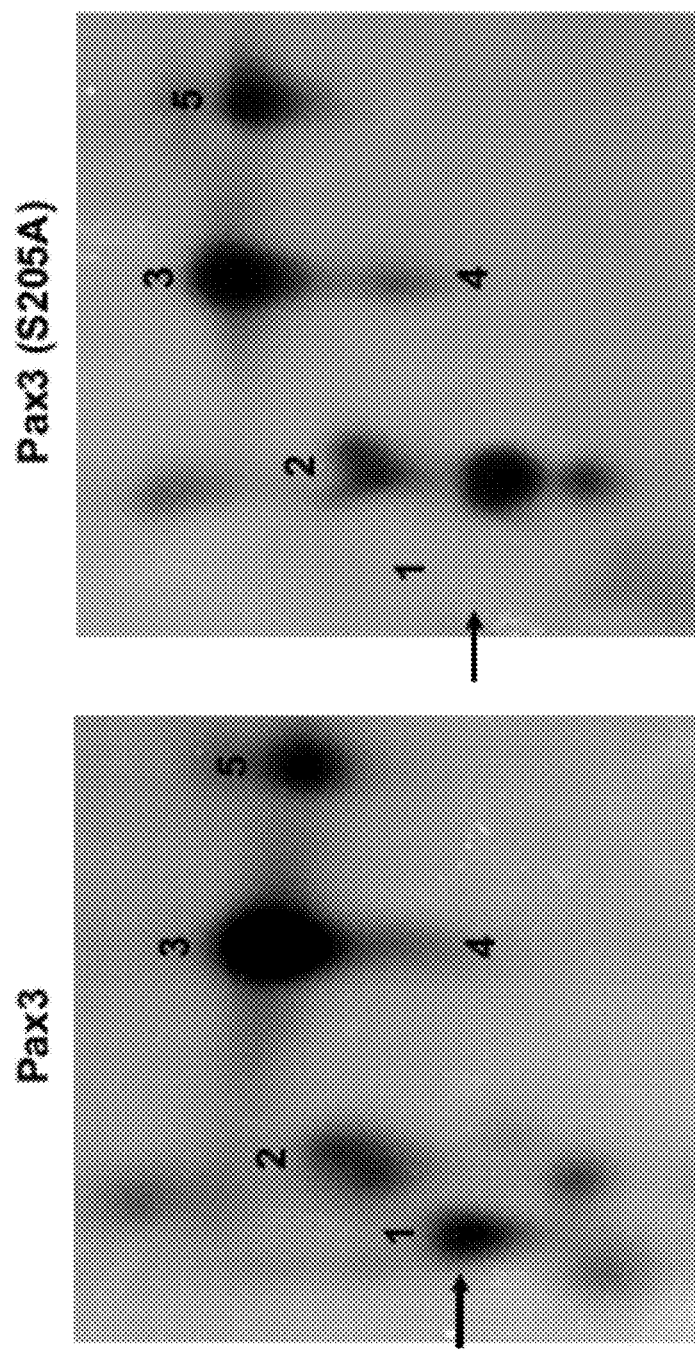
FIG. 8 illustrates the results of two-dimensional phosphopeptide analysis of wildtype Pax3 and Pax3 S205A. Bacterially-expressed GST-Pax3 and GST-Pax3 S205A were phosphorylated in vitro, trypsinized using TPCK-trypsin, and analyzed by two-dimensional phosphopeptide analysis. The arrow indicates the phosphopeptide that is no longer phosphorylated when the point mutation is serine 205.

A subsequent two-dimensional phosphopeptide analysis gave results consistent with the observed decrease in overall phosphorylation. Bacterially expressed GST-Pax3 and GST-Pax3 S205A were phosphorylated in vitro, trypsinized using TPCK-trypsin, and analyzed by two-dimensional phosphopeptide analysis, as described above. The results are shown in FIG. 8. The arrow indicates the phosphopeptide that was no longer phosphorylated upon the mutation of serine 205. Pax3 (S205A) has a complete loss of phosphorylation relative to wildtype Pax3, as shown by the loss of the single spot "1" in FIG. 8. Taken together, these results confirm serine 205 as a site of phosphorylation on Pax3 in vitro.

EXAMPLE 6

Identification of Ser205 as a Site of Pax3 Phosphorylation In Vivo

To facilitate the in vivo confirmation and biological analysis of phosphorylation at serine 205, an antibody specific for Pax3 only when Pax3 is phosphorylated at serine 205 was raised as described above. In order to confirm the specificity of this antibody, a Western blot analysis with the anti-Pax3 (p205) antibody was performed on bacterially expressed and purified GST-Pax3 and GST-Pax3(S205A) that had been phosphorylated using our in vitro kinase assay. Equal amounts of bacterially expressed and purified GST-Pax3 and three GST-Pax3 phospho-incompetent point mutants were used in independent in vitro kinase assays using [$^{32}$P]-ATP to confirm phosphorylation or with cold ATP. The proteins that were non-radioactively labeled were subsequently used for Western blot analysis using the anti-Pax3(p205). As shown in FIG. 9A, top panel, Coomassie staining demonstrated equal amounts of protein. An independent radiolabeling experiment confirmed that the efficient phosphorylation of Pax3 is dependent on the presence of serine 205 (FIG. 9A, middle panel). Consistent with the phosphorylation of Pax3 at serine 205, the antibody showed a strong reactivity only when Pax3 was capable of being phosphorylated at Ser205 (FIG. 9A, bottom panel). In FIG. 9A, the arrows indicate the mobility of wildtype Pax3 while the asterisks indicate the mobility of the phospho-incompetent point mutants. These results confirmed the specificity of the antibody for Pax3 when phosphorylated at serine 205.

To confirm that serine 205 is a site of phosphorylation on Pax3 in vivo, a Western blot analysis was performed on total cell extracts from proliferating mouse primary myoblasts, which have been demonstrated to endogenously express Pax3 (Miller and Hollenbach 2007). The analysis was performed using the previously described monospecific Pax3 antibody (Lam et al. 1999) and the new anti-Pax3(p205) antibody. The Western blot analysis was performed on 50 µg of total cell extract using either the general anti-Pax3 antibody (left panel) or anti-Pax3(p205) antibody (right panel). Consistent with previous reports (Miller and Hollenbach 2007), the general Pax3 antibody identified two distinctly migrating species with apparent molecular weights of 56 kD and 66 kD (FIG. 9B, left panel). However, a Western blot analysis using the anti-Pax3(p205) antibody on the identical membrane reacted solely with the apparent 66 kD species (FIG. 9B, right panel). This result not only conclusively demonstrates that Pax3 is phosphorylated at serine 205 in proliferating mouse primary myoblasts, but that this phosphorylation event changes the electrophoretic mobility of Pax3.

EXAMPLE 7

Phosphorylation at Serine 205 is Rapidly Lost Upon Myogenic Differentiation

To determine if Pax3 is phosphorylated throughout myogenic differentiation, proliferating mouse primary myoblasts were induced to differentiate for 0-20 hours (FIG. 10A) or for 0-4 hours (FIG. 10B), as described above. Total cell extracts were created from the differentiated myoblasts at the indicated time points, and a standard Western blot analysis was performed on 50 µg of total cell extract using the anti-Pax3 antibody (top panels) or the anti-Pax3(p205) antibody (bottom panels). Two distinctly migrating species of Pax3 in proliferating primary myoblasts were observed, of which only the apparent 66 kD species was phosphorylated at serine 205 (FIGS. 10A and 10B). The complete loss of expression of Pax3 within twenty-four hours of differentiation was observed, as previously described (Miller and Hollenbach 2007). More importantly, within four hours of the induction of myogenic differentiation, the complete loss of the apparent 66 kD species and the corresponding reactivity of the anti-Pax3(p205) antibody was observed (FIG. 10A). To further characterize this change in phosphorylation, the differentiation experiment was repeated using earlier time points. Surprisingly, a complete loss of the apparent 66 kD species and reactivity with the anti-Pax3(p205) antibody was observed by fifteen minutes of differentiation. These results are the first to demonstrate that phosphorylation of Pax3 at serine 205 is rapidly abolished upon the induction of myogenic differentiation.

Because the loss of phosphorylation of Pax3 at serine 205 resembles what is known for MyoD and myogenin, the observed change in Pax3 phosphorylation may alter the biological activity of Pax3 as the myoblasts begin to differentiate. Although the exact mechanism by which phosphorylation regulates Pax3 is not known, the position of this phosphorylated amino acid within the primary amino acid structure strongly indicates a possible effect on the biological activities of Pax3. Serine 205 is located adjacent to the octapeptide domain (FIG. 7A) and is present in the region of Pax3 demonstrated to mediate protein-protein interactions with the transcriptional regulators hDaxx (Hollenbach et al. 1999), calmyrin (Hollenbach et al. 2002) and HIRA (Magnaghi et al. 1998). Phosphorylation of transcription factors is a common mechanism used to regulate protein-protein interactions. Therefore, the phosphorylation status of serine 205 may control the interaction of Pax3 with these and other cofactors thereby regulating such biological activities as transcriptional activation.

Although serine 205 may not be the only site of phosphorylation, the above results suggest that this site may be the primary site of phosphorylation. Phosphorylation occurred only in the region of Pax3 surrounding the octapeptide domain (FIGS. 6 and 7A). If all of the amino acids were to be phosphorylated independent of each other, then mutation of a single site, such as serine 205, should not alter subsequent phosphorylation events. Therefore, mutation of a single site would not be expected to significantly alter the global phosphate radiolabeling of Pax3 using the in vitro kinase assay. However, mutation of serine 205 to an alanine resulted in an approximately 80-90% loss of global phosphate radiolabeling of Pax3 (FIG. 7C). Taken together these results indicate that the inability of Pax3 to be phosphorylated at serine 205 greatly reduces the efficiency of phosphorylation at additional sites. In this manner, serine 205 would act as the primary site of phosphorylation on Pax3 that then regulates subsequent phosphorylation events.

Using similar procedures, the temporal expression of Pax3-FOXO1 and phosphorylated Pax3-FOXO1(p205) were followed. (See Example 12 below). FIGS. 11A and 11B show the temporal expression of Pax3 and its phosphorylated form (Pax3(p205)) (FIG. 11A) and of Pax3-FOXO1 and its phosphorylated form (Pax3-FOXO1(p205)) (FIG. 11B). Also shown is the temporal expression of the muscle determination factors of MyoD, Myf5, and myogenin, which control the progression through myogenesis with the terminal differentiation being marked by the expression of myosin heavy chain. In comparing FIGS. 11A and 11B, it is seen that the expression of Pax3-FOXO1 and phosphorylated Pax3-FOXO1(p205) continue throughout myogenesis in contrast to the brief expression of Pax3 and phosphorylated Pax3 (p205). Without wishing to be bound by this theory, we believe that the altered biological activities of the fusion protein contribute to the inability of myoblasts to achieve terminal differentiation. The improperly regulated increased transcriptional activity of Pax3-FOXO1 would allow the unfettered, enhanced expression of genes such as c-Met and IGF-I-R. The ability of the fusion protein to bind to and activate non-Pax3 regulated gene promoters would also induce the expression of genes such as PDGFαR. Combined with the aberrant phosphorylation and expression of Pax3-FOXO1 in the late stages of myogenic differentiation, these altered functions would drive the improper expression of genes normally expressed in proliferating cells that are important for cellular growth and have been demonstrated to inhibit differentiation.

EXAMPLE 8

Identification of Ser201, 205, and 209 as In Vitro Sites of Phosphorylation

Figure 12:
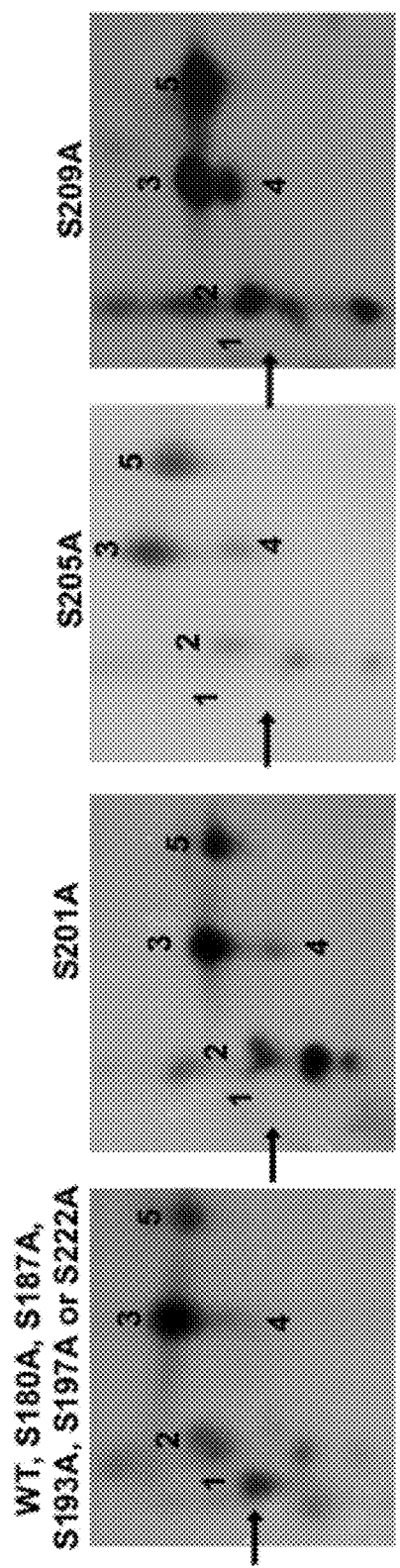
FIG. 12 illustrates the results of two-dimensional phosphopeptide analysis of the GST-Pax3 point mutants at S201, S205, and S209. The left panel is a representative analysis for wild type Pax3 (WT) and additional point mutants at S180, S187, S193, S197, and S222. The arrow indicates the radiolabeled peptide lost upon mutation of the serines at 201, 205 and 209.

As shown above, Pax3 was demonstrated to be phosphorylated only on serines surrounding the octapeptide domain, and that Pax3 was phosphorylated on serine 205 in vitro. Additional phosphorylation sites on Pax3 were also shown. Therefore, each of the remaining seven serines in this region of GST-Pax3 were individually mutated to nonphosphorylatable alanines (S180A, S187A, S193A, S197A, S201A, and S209A), and these bacterially expressed and purified proteins were used in the semi-in vitro kinase assay followed by two-dimensional phosphopeptide analysis, as described above. Mutation of Ser205 to the non-phosphorylateable alanine resulted in the complete loss of a single radiolabeled peptide (FIG. 12, peptide 1). The individual mutation of either Ser201 or Ser209 also resulted in the loss of this same radiolabeled peptide (FIG. 12, peptide 1), a loss that was not observed for the remaining point mutants (FIG. 12, left panel). These data indicate that Pax3 is phosphorylated at Ser201 and Ser209 in vitro.

Figure 13:
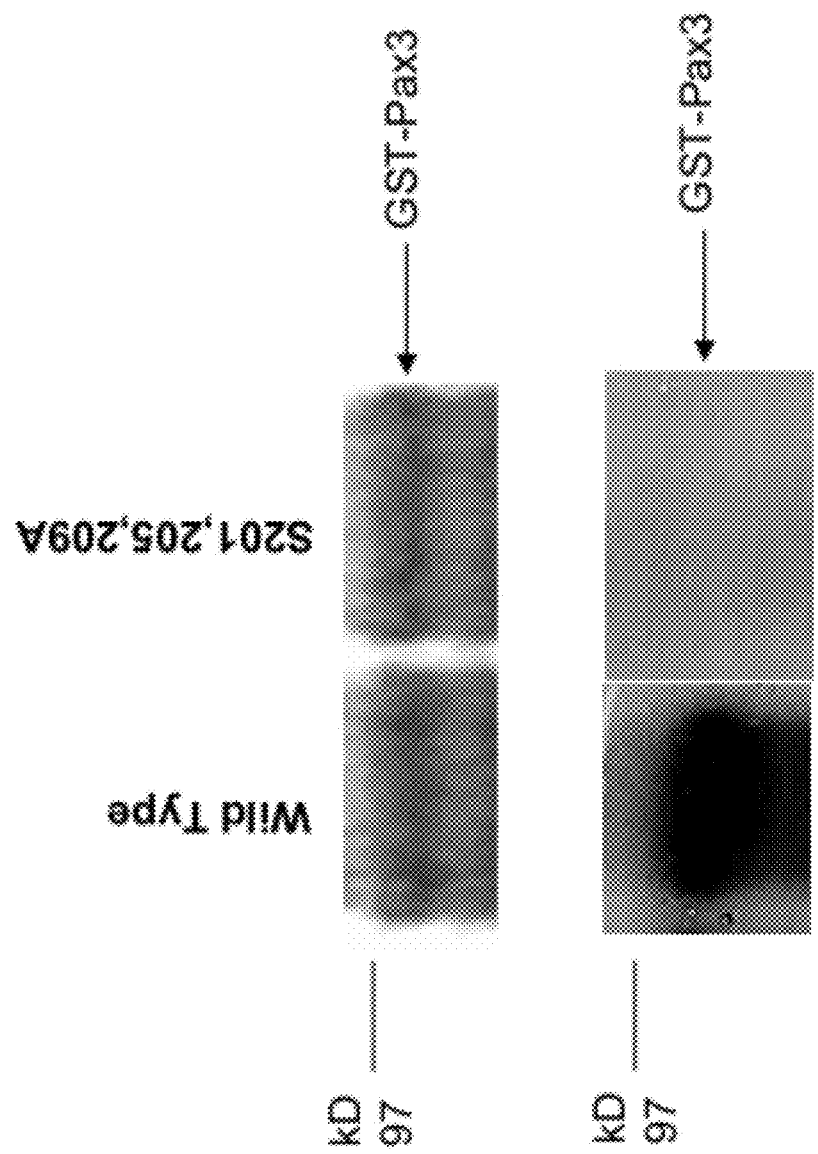
FIG. 13 illustrates the results of phosphorylation of wildtype GST-Pax3 (left lane) and the GST-Pax3 triple mutant, with the top panel showing the results of a Coomassie stained gel.

To confirm that Ser201, Ser205, and Ser209 are sites of phosphorylation, a triple non-phosphorylatable GST-Pax3 mutant was created in which all three of these serines were mutated to alanines (S201:205:209A). The bacterially expressed and purified protein was used in the semi-in vitro kinase assay described above. Mutation of these three serines completely abolished the ability of Pax3 to be phoshorylated, as shown in FIG. 13, which indicates that Ser201, Ser205, and Ser209 are the only sites of Pax3 phosphorylation in vitro.

EXAMPLE 9

Phosphorylation of Ser205 is Required for Additional Phosphorylation Events

Figure 14:
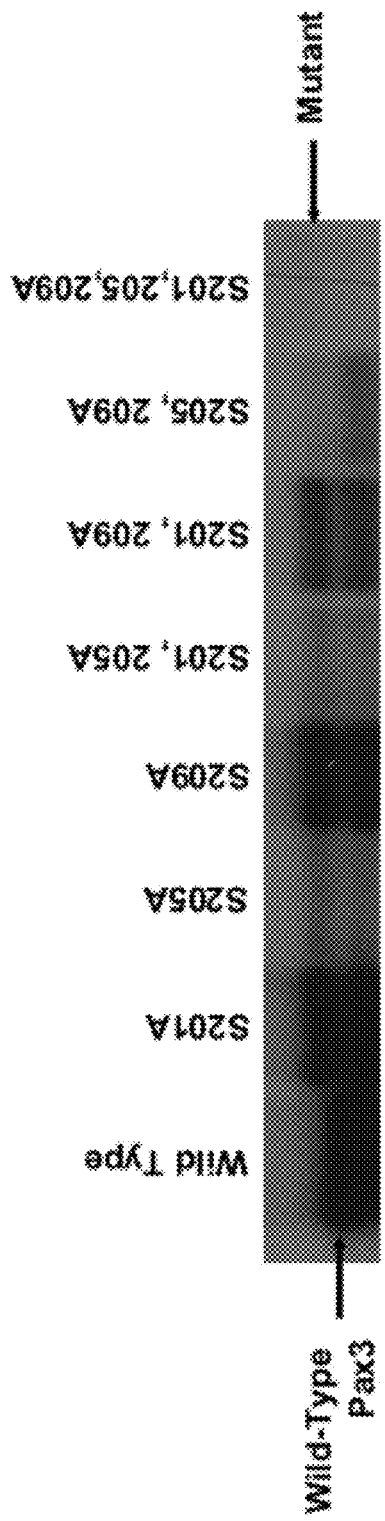
FIG. 14 illustrates the results of phosphorylation of GST-Pax3 wildtype and the GST-Pax3 single (S201A, S205A, and S209A), double (S201A, S205A; S201A, S209A; and S205A, S209A), and triple mutants (S201A, S205A, S209A), which demonstrates the primacy of phosphorylation at Ser205, and when combined with FIG. 13 illustrates that Ser201, Ser205, and Ser209 are the only sites of phosphorylation on Pax3.

In addition to identifying the in vitro sites of phosphorylation, the above results indicate that phosphorylation of Ser205 is required for the subsequent phosphorylation of Ser201 and Ser209. This statement is based on the following observation. If the three sites were phosphorylated independent of each other, a similar level of radiolabel incorporation would be expected for each of the single or double mutants in our semi-in vitro kinase assay. FIG. 14 shows the relative intensity of phosphorylation of GST-Pax3 and the GST-Pax3 single (S201A, S205A, and S209A), double (S201,205A; S201,205A; and S205,209A) and triple (S201,205,209A) mutations. The mutation of Ser205, in any combination, resulted in about 80-90% loss of radiolabeled phosphorylation of Pax3 (FIG. 14). Therefore, loss of phosphorylation at Ser205 greatly reduces the efficiency of phosphorylation at Ser201 and Ser209 suggesting that phosphorylation of Ser205 is required for the efficient phosphorylation of Ser201 and/or Ser209.

EXAMPLE 10

Pax3 is Phosphorylated at Ser205 and Ser209 In Vivo

Figure 15:
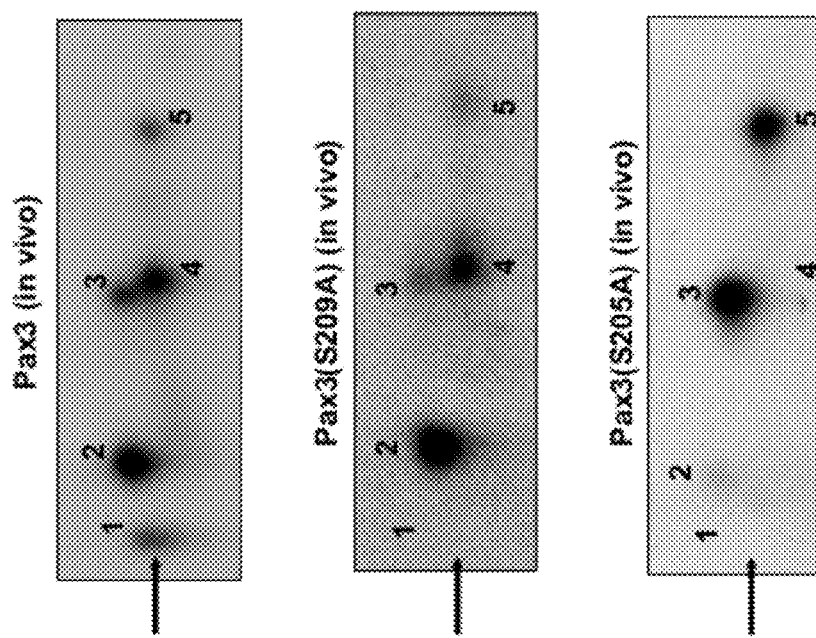
FIG. 15 illustrates the results of phosphopeptide and Western blot analysis showing the identification of Ser209 as an in vivo site of Pax3 phosphorylation. The top panel shows wildtype Pax3 phosphopeptide map, the middle panel shows the Pax3(S209A) phosphopeptide map, and the bottom panel shows the Pax3(S205A) phosphopeptide map as a control.

By phosphopeptide and Western blot analysis using an antibody specifically recognizing Pax3 when phosphorylated at Ser205 (anti-Pax3[p205]) as described above, Ser205 was shown to be a site of Pax3 phosphorylation in proliferating primary myoblasts. To confirm that Ser209 is phosphorylated in vivo, primary myoblasts were stably transduced with FLAG-epitope tagged phospho-incompetent Pax3 point mutant (S209A) as described above and a phosphopeptide map of this mutant was created. As seen with the S205A mutant (FIG. 15, bottom panel), mutation of Ser209 resulted in the primary loss of peptide 1 from the in vivo map (FIG. 15, middle panel) identical to the radiolabeled peptide lost upon mutation of these sites in the in vitro kinase assays (FIG. 8). In addition, the S205A mutant was shown to primarily retain the peptides corresponding to a single phosphorylation event (FIG. 15). Taken together, these results demonstrate that Ser209 is a site of phosphorylation on Pax3 in proliferating primary myoblasts and supports that phosphorylation of Ser205 is required to regulate at least one subsequent phosphorylation event.

EXAMPLE 11

Phosphorylation at Ser205 by Casein Kinase II (CKII) Promotes Pax3 DNA Binding

Figure 16:
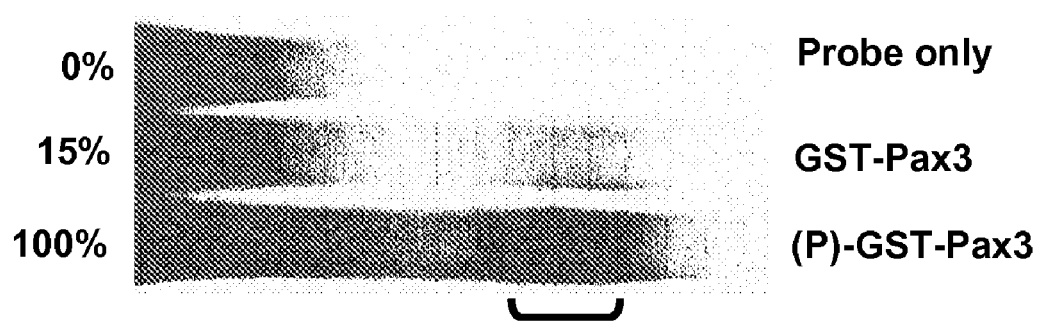
FIG. 16 illustrates the results of electromobility shift analysis (EMSA) using GST-Pax3 or GST-Pax3 maximally phosphorylated with CKII ([P]-GST-Pax3]). The bracket indicates the Pax3-dependent shift and the percent maximal binding relative to the phosphorylated species determined by densitometric analysis is indicated.

We have shown that purified CKII phosphorylated Pax3 and Pax3-FOXO1 at Ser205 (data not shown). To examine the effect of phosphorylation of Pax3 at Ser205 by CKII on DNA binding, GST-Pax3 was maximally phosphorylated with CKII in vitro using non-radiolabeled ATP. The non-phosphorylated negative control and phosphorylated GST-Pax3 were eluted from the resin and equal amounts of purified protein were used in an electromobility shift analysis (EMSA) with a radiolabeled oligonucleotide that contains both paired- and homeodomain DNA recognition sequences. FIG. 16 shows the result of the EMSA, with the bracket indicating the Pax3-dependent shift. The percent maximal binding relative to the phosphorylated species, as determined by densitometric analysis is given in FIG. 16. Phosphorylation of Pax3 at Ser205 by CKII resulted in a nearly 10-fold increase in Pax3 DNA binding (FIG. 16). This result provides direct biological relevance that phosphorylation of Pax3 at Ser205 by CKII enhances DNA binding.

EXAMPLE 12

Figure 17:
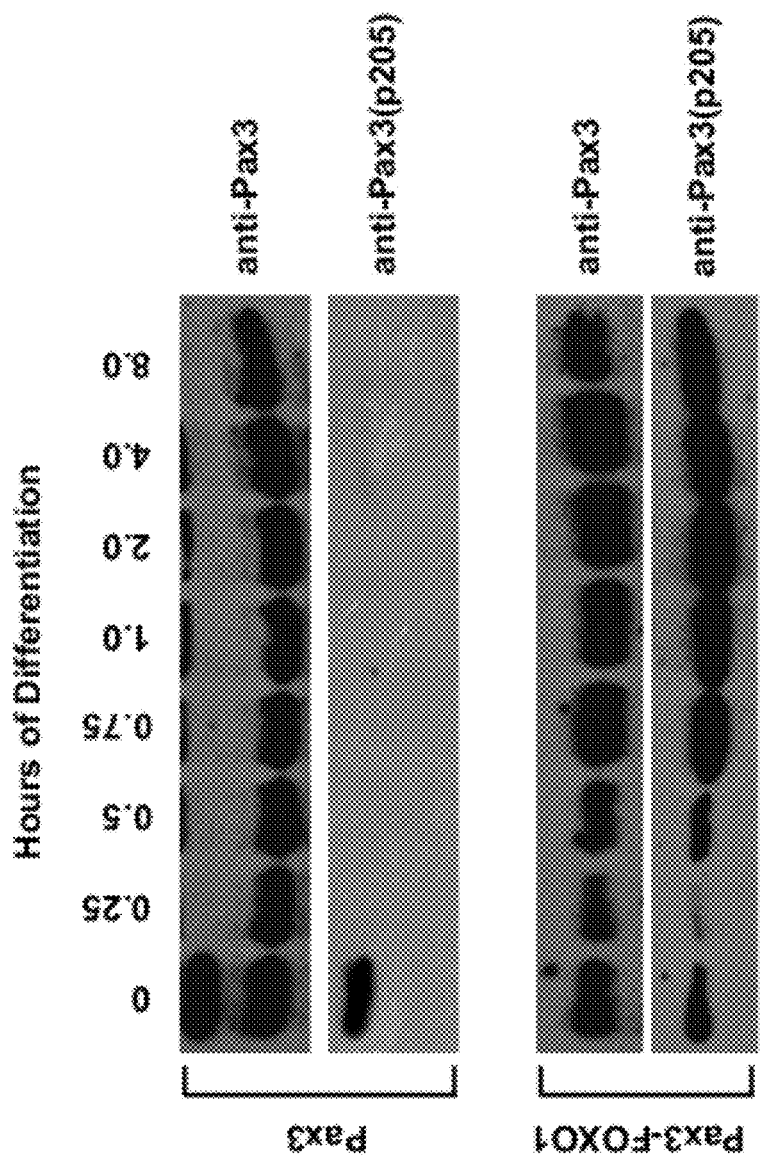
FIG. 17 illustrates the results of Western blot analysis showing the changes in phosphorylation of Ser205 on Pax3 (top panels) and Pax3-FOXO1 (bottom panels) upon the induction of myogenic differentiation.

Loss of Phosphorylation at Ser205 on Pax3 but not Pax3-FOXO1 Upon the Induction of Myogenic Differentiation As shown above, Pax3 is phosphorylated at Ser205 in proliferating primary myoblasts, and this phosphorylation event alters the electrophoretic mobility of Pax3. Phosphorylation of Pax3 at Ser205 was also shown to be rapidly lost upon the induction of myogenic differentiation. To determine the phosphorylation status of Ser205 on Pax3-FOXO1 during differentiation, primary myoblasts stably expressing the fusion protein were induced to differentiate, as described above, and total cell extracts were collected at various times during differentiation. Equal amounts (50 µg) of total cell extract from each time point were separated by 8% SDS-PAGE and subsequently used for a Western blot analysis using the general Pax3 antibody or the anti-Pax3(p205) antibody, as described above. As illustrated in FIG. 17, Pax3-FOXO1 is phosphorylated at Ser205 in proliferating primary myoblasts. However, in direct contrast to the results observed for Pax3, Pax3-FOXO1 is phosphorylated at Ser205 throughout myogenic differentiation (FIG. 17). This result provides direct evidence that Pax3-FOXO1 is phosphorylated at Ser205 and that the pattern of phosphorylation differs significantly from wild type Pax3 throughout myogenic differentiation. This difference is also illustrated in FIGS. 11A and 11B. This data strongly indicates that changes in phosphorylation are important for the regulation of Pax3 during myogenic differentiation.

EXAMPLE 13

Figure 18:
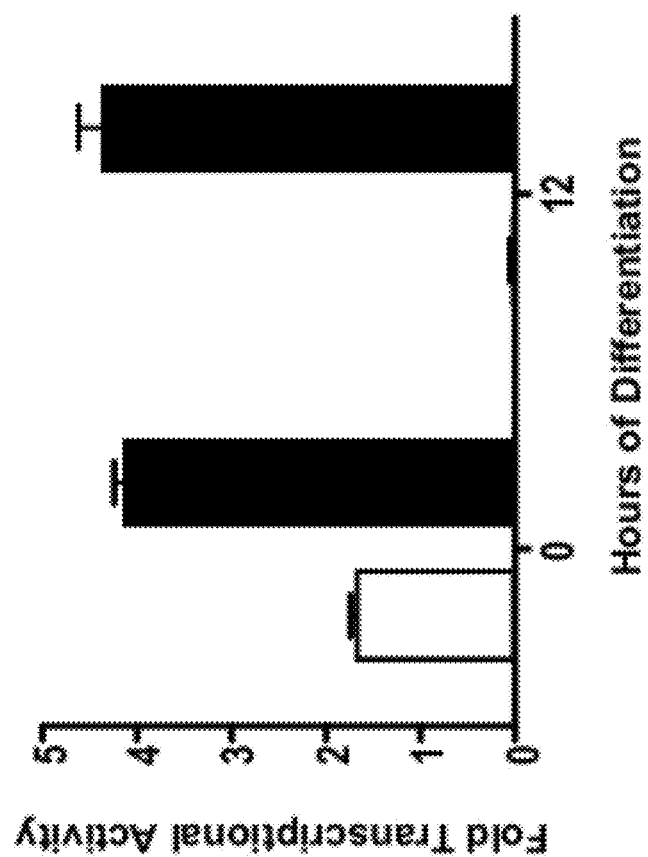
FIG. 18 illustrates the transcriptional activity as determined using a radioactive chloramphenicol acetyl transferase (CAT) assay of Pax3 (white bars) and Pax3-FOXO1 (black bars) during myogenic differentiation. All samples were normalized for transcription efficiency and are expressed as fold activity relative to background. The error bars represent the standard deviation from four independent determinations.

The Transcriptional Activity of Pax3 and Pax3-FOXO1 Correlate to their Phosphorylation Status During Myogenic Differentiation As shown above, phosphorylation of Pax3 at Ser205 (FIG. 16) promotes DNA binding. In addition, phosphorylation of Pax3-FOXO1 has been shown to promote DNA binding (Amstutz et al. 2008). To determine if the observed differences in phosphorylation of Pax3 and Pax3-FOXO1 (FIG. 17) correlate with transcriptional activity during myogenic differentiation, primary myoblasts stably transduced with either Pax3 or Pax3-FOXO1 were transfected with a Pax3-specific transcriptional reporter construct, (PRS-9)TK-CAT, which contains six tandem repeats of the Pax3 paired and homeodomain recognition sequence upstream of the chloramphenicol acetyl transferase (CAT) gene. Twelve hours post-transfection, the myoblasts were induced to differentiate, as described above, and cells at the indicated time points were harvested, lysed, and the transcriptional activity was determined using a radioactive CAT assay. FIG. 18 shows the transcriptional activity of Pax3 (white bars) and Pax3-FOXO1 (black bars) during myogenic differentiation. In FIG. 18, all samples were normalized for transcription efficiency and, the data expressed as fold activity relative to background. The error bars represent the standard deviation from four independent determinations. Approximately 2-fold and 4-fold increase in transcriptional activity was observed relative to background for Pax3 and Pax3-FOXO1, respectively, in proliferating primary myoblasts. After twelve hours of differentiation, a time point when both Pax3 is expressed but not phosphorylated, a complete loss of Pax3 transcriptional activity was observed (FIG. 18), consistent with the complete loss of phosphorylation upon the induction of differentiation (FIG. 17). In contrast, no significant change in the transcriptional activity of Pax3-FOXO1 was seen (FIG. 18), a result in keeping with the presence of phosphorylation of Pax3-FOXO1 throughout early myogenic differentiation (FIG. 17). Therefore, these results provide evidence that a strong correlation exists between the phosphorylation status and transcriptional activity of Pax3 and Pax3-FOXO1 during myogenic differentiation.

EXAMPLE 14

Endogenous Pax3-FOXO1 is Phosphorylated at Ser205 in the ARMS Tumor Cell Line RH30

To determine the phosphorylation status of Pax3-FOXO1 in the ARMS tumor cell line RH30, which contains the (2; 13) chromosomal translocation and expresses endogenous Pax3-FOXO1, 50 µg of total cell extract were separated by 8% SDS-PAGE and analyzed by Western blot analysis with the general Pax3 antibody, as discussed above. After stripping, the same blot was subsequently probed with the anti-Pax3 (p205) antibody. FIG. 19 shows the results. Consistent with the results above in primary myoblasts, endogenous Pax3-FOXO1 is phosphorylated at Ser205 in the ARMS tumor cell line RH30 (FIG. 19).

REFERENCES

Amstutz, R., Wachtel, M., Heinz, T., Kleinert, P., Ebauer, M., Haneke, T., Oehler-Jänne, C., Fabbro, D., Niggli, F. K., and Schäfer, B. W. 2008. Phosphorylation regulates transcriptional activity of PAX3/FKHR and reveals novel therapeutic possibilities. *Cancer Res.* 68: 3767-3776.
Boutet, S. C., Disatnik, M. H., Chan, L. S., Iori, K., and Rando, T. A. 2007. Regulation of Pax3 by proteasomal degradation of monoubiquitinated protein in skeletal muscle progenitors. *Cell* 130: 349-362.
Boyle, W. J., van der Geer, P., and Hunter, T. 1991. Phosphopeptide mapping and phosphoamino acid analysis by two-dimensional separation on thin-layer cellulose plates. *Methods Enzymol* 201: 110-149.
Buckingham, M., and Relaix, F. 2007. The role of Pax genes in the development of tissues and organs: Pax3 and Pax7 regulate muscle progenitor cell functions. *Annual review of cell and developmental biology* 23: 645-673.
Epstein, J. A., Shapiro, D. N., Cheng, J., Lam, P. Y., and Maas, R. L. 1996. Pax3 modulates expression of the c-Met receptor during limb muscle development. *Proc Natl Acad Sci USA* 93: 4213-4218.
Ho, S. N., Hunt, H. D., Horton, R. M., Pullen, J. K., and Pease, L. R. 1989. Site-directed mutagenesis by overlap extension using the polymerase chain reaction. *Gene* 77: 51-59.
Hollenbach, A. D., McPherson, C. J., Lagutina, I., and Grosveld, G. 2002. The EF-hand calcium-binding protein calmyrin inhibits the transcriptional and DNA-binding activity of Pax3. *Biochim Biophys Acta* 1574: 321-328.
Hollenbach, A. D., Sublett, J. E., McPherson, C. J., and Grosveld, G. 1999. The Pax3-FKHR oncoprotein is unresponsive to the Pax3-associated repressor hDaxx. *Embo J* 18: 3702-3711.
Hunter, T., and Karin, M. 1992. The regulation of transcription by phosphorylation. *Cell* 70: 375-387.
Kitzmann, M., Vandromme, M., Schaeffer, V., Carnac, G., Labbe, J. C., Lamb, N., and Fernandez, A. 1999. cdk1- and cdk2-mediated phosphorylation of MyoD Ser200 in growing C2 myoblasts: role in modulating MyoD half-life and myogenic activity. *Mol Cell Biol* 19: 3167-3176.
Laker, C., Meyer, J., Schopen, A., Friel, J., Heberlein, C., Ostertag, W., and Stocking, C. 1998. Host cis-mediated extinction of a retrovirus permissive for expression in embryonal stem cells during differentiation. *Journal of virology* 72: 339-348.
Lam, P. Y., Sublett, J. E., Hollenbach, A. D., and Roussel, M. F. 1999. The oncogenic potential of the Pax3-FKHR fusion protein requires the Pax3 homeodomain recognition helix but not the Pax3 paired-box DNA binding domain. *Mol Cell Biol* 19: 594-601.
Li, L., Zhou, J., James, G., Heller-Harrison, R., Czech, M. P., and Olson, E. N. 1992. FGF inactivates myogenic helix-loop-helix proteins through phosphorylation of a conserved protein kinase C site in their DNA-binding domains. *Cell* 71: 1181-1194.
Magnaghi, P., Roberts, C., Lorain, S., Lipinski, M., and Scambler, P. J. 1998. HIRA, a mammalian homologue of *Saccharomyces cerevisiae* transcriptional co-repressors, interacts with Pax3. *Nat Genet* 20: 74-77.
Maroto, M., Reshef, R., Munsterberg, A. E., Koester, S., Goulding, M., and Lassar, A. B. 1997. Ectopic Pax-3 activates MyoD and Myf-5 expression in embryonic mesoderm and neural tissue. *Cell* 89: 139-148.
Miller, P. J., and Hollenbach, A. D. 2007. The oncogenic fusion protein Pax3-FKHR has a greater post-translational stability relative to Pax3 during early myogenesis. *Biochimica et biophysica acta* 1770: 1450-1458.
Rando, T. A., and Blau, H. M. 1997. Methods for myoblast transplantation. *Methods in cell biology* 52: 261-272.
Swift, S., Lorens, J., Achacoso, P., and Nolan, G. P. 1999. Rapid production of retroviruses for efficient gene delivery to mammalian cells using 293T cell-based systems. In *Current Protocols in Immunology*. (eds. J. E. Coligan, A. M. Kruisbeek, D. H. Margulies, E. M. Shevach, and W. Strober), pp. 10.17. John Wiley and Sons, Boston, Mass.
Tajbakhsh, S., and Buckingham, M. 2000. The birth of muscle progenitor cells in the mouse: spatiotemporal considerations. *Current topics in developmental biology* 48: 225-268.
Williams, B. A., and Ordahl, C. P. 1994. Pax-3 expression in segmental mesoderm marks early stages in myogenic cell specification. *Development (Cambridge, England)* 120: 785-796.
Xia, S. J., and Barr, F. G. 2005. Chromosome translocations in sarcomas and the emergence of oncogenic transcription factors. *Eur J Cancer* 41: 2513-2527.

The complete disclosures of all references cited in this application are hereby incorporated by reference. Also incorporated by reference is the complete disclosure of the following which is attached as Appendix A: P. J. Miller et al., "Identification of serine 205 as a site of phosphorylation on Pax3 in proliferating but not differentiating primary myoblasts," Protein Science, vol. 17, pp. 1979-1986 (2008). In the event of an otherwise irreconcilable conflict, however, the present specification shall control.

What is claimed:

1. An isolated antibody or antigen-binding portion thereof that specifically binds to Pax3 having a phosphorylated serine amino acid at a position in SEQ ID NO:1 selected from the group consisting of position 201, position 205, and position 209, and that does not bind to Pax3 without a phosphorylated serine amino acid.

2. The antibody or antigen-binding portion thereof as in claim 1, wherein the phosphorylated serine amino acid of Pax3 is at position 205 as in SEQ ID NO: 1.

3. The antibody or antigen-binding portion thereof as in claim 1, wherein the phosphorylated serine amino acid of Pax3 is at position 201 as in SEQ ID NO: 1.

4. The antibody or antigen-binding portion thereof as in claim 1, wherein the phosphorylated serine amino acid of Pax3 is at position 209 as in SEQ ID NO: 1.

5. The antibody or antibody fragment of claim 1, wherein the antibody is a polyclonal antibody.

6. A kit for use in identifying the amount of phosphorylated Pax3 in a sample, said kit comprising one or more antibodies or antigen-binding fragments of claim 1.

7. A kit for use in identifying the amount of phosphorylated Pax3-FOXO1 fusion protein in a sample, said kit comprising one or more antibodies or antigen-binding fragments of claim 1.

8. A method for measuring an amount of phosphorylated Pax3 in a biological sample, said method comprising the steps:
   (a) adding to the sample an isolated antibody or an antigen-binding fragment thereof as in claim 1 and a labeled bioactive phosphorylated Pax3;
   (b) allowing the phosphorylated Pax3 in the sample and labeled bioactive phosphorylated Pax3 to compete for and specifically bind with binding sites on said antibody; and
   (c) measuring the amount of labeled phosphorylated Pax3 which specifically bound to the antibody to determine the amount of phosphorylated Pax3 in said sample.

9. A method for measuring an amount of phosphorylated Pax3-FOXO1 in a biological sample, said method comprising the steps:
   (a) adding to the sample an isolated antibody or an antigen-binding fragment thereof as in claim 1 and a labeled bioactive phosphorylated Pax3-FOXO1;
   (b) allowing the phosphorylated Pax3-FOXO1 in the sample and labeled bioactive phosphorylated Pax3-FOXO1 to compete for and specifically bind with binding sites on said antibody; and
   (c) measuring the amount of labeled phosphorylated Pax3-FOXO1 which specifically bound to the antibody to determine the amount of phosphorylated Pax3-FOXO1 in said sample.

10. A method to screen drugs that decrease or increase the phosphorylation of Pax3 in a mammalian cell or tissue in which Pax3 is intrinsically expressed or overexpressed, said method, comprising the steps of:
   (a) incubating the cells or tissue with a candidate drug for a time sufficient to test the activity of a drug on this cell or tissue;
   (b) homogenizing the cells after incubation to obtain a homogenate;
   (c) incubating the obtained homogenate with an antibody specific for Pax3 to form an immunoprecipitate; and
   (d) detecting the presence or absence of a phosphorylated Pax3 protein by reacting the immunoprecipitate with the isolated antibody or antigen-binding fragment thereof as in claim 1 detecting specific binding with the phosphorylated Pax3 and then and comparing the amount of phosphorylated Pax3 with an amount measured in a cell or tissue that was not incubated with the candidate drug.

11. A method to screen drugs that decrease or increase the phosphorylation of Pax3-FOXO1 fusion protein in a mammalian cell or tissue in which Pax3-FOXO1 is intrinsically expressed or overexpressed, said method, comprising the steps of:
   (a) incubating the cells or tissue with a candidate drug for a time sufficient to test the activity of a drug on this cell or tissue;
   (b) homogenizing the cells after incubation to obtain a homogenate;
   (c) incubating the obtained homogenate with an antibody specific for Pax3-FOXO1 fusion protein to form an immunoprecipitate; and
   (d) detecting the presence or absence of a phosphorylated Pax3-FOXO1 protein by reacting the immunoprecipitate with the isolated antibody or antigen-binding fragment thereof as in claim 1 detecting specific binding with the phosphorylated Pax3-FOXO1 and then and comparing the amount of phosphorylated Pax3-FOXO1 protein with an amount measured in a cell or tissue that was not incubated with the candidate drug.

* * * * *

UNITED STATES PATENT AND TRADEMARK OFFICE
CERTIFICATE OF CORRECTION

PATENT NO. : 8,304,521 B2
APPLICATION NO. : 12/477541
DATED : November 6, 2012
INVENTOR(S) : A. Hollenbach et al.

Page 1 of 1

It is certified that error appears in the above-identified patent and that said Letters Patent is hereby corrected as shown below:

Col. 1, line 8, please replace "contract No. 1 P20 RR0201 52-01" with
--contracts No. 1 P20 RR0201 52-01 and No. R01 CA138656--

Signed and Sealed this
Fifth Day of February, 2013

Teresa Stanek Rea
*Acting Director of the United States Patent and Trademark Office*

UNITED STATES PATENT AND TRADEMARK OFFICE
CERTIFICATE OF CORRECTION

| | | |
|---|---|---|
| PATENT NO. | : 8,304,521 B2 | Page 1 of 1 |
| APPLICATION NO. | : 12/477541 | |
| DATED | : November 6, 2012 | |
| INVENTOR(S) | : Hollenbach et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 325 days.

Signed and Sealed this
Second Day of September, 2014

Michelle K. Lee
*Deputy Director of the United States Patent and Trademark Office*